(12) United States Patent
Esaki et al.

(10) Patent No.: US 7,115,735 B2
(45) Date of Patent: Oct. 3, 2006

(54) DEHYDROGENASE AND A GENE ENCODING THE SAME

(75) Inventors: Nobuyoshi Esaki, Shiga (JP); Hisaaki Mihara, Kyoto (JP); Mari Hara, Yokohama (JP); Makoto Ueda, Yokohama (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 10/927,028

(22) Filed: Aug. 27, 2004

(65) Prior Publication Data

US 2005/0124040 A1   Jun. 9, 2005

Related U.S. Application Data

(63) Continuation-in-part of application No. PCT/JP03/02204, filed on Feb. 27, 2003.

(30) Foreign Application Priority Data

Feb. 28, 2002 (JP) .................. JP2002-054198

(51) Int. Cl.
   *C07D 267/02* (2006.01)
   *A61K 31/55* (2006.01)

(52) U.S. Cl. ............... 540/544; 548/950; 514/211.01; 435/179

(58) Field of Classification Search ........... 540/544; 548/950; 435/179

See application file for complete search history.

(56) References Cited

U.S. PATENT DOCUMENTS 5,942,630 A    8/1999    Barth et al.

FOREIGN PATENT DOCUMENTS

| EP | 254354 | 1/1988 |
| JP | 57-183799 | 11/1982 |
| JP | 60-218400 | 11/1985 |

OTHER PUBLICATIONS

Hester et al., "Purification of *Pseudomonas putida* branched-chain keto acid dehydrogenase E1 component", Methods Enzymology, vol. 324, pp. 129-138 (2000).

Hester et al., "Purification of active E1 α2β2 of *Pseudomonas putida* branched-chain-oxoacid dehydrogenase", Eur. J. Biochem., vol. 233, pp. 828-836 (1995).

Rae et al., "Sequences and expression of pyruvate dehydrogenase from *Pseudomonas aeruginosa*", J. Bacteriology, vol. 179, pp. 3561-3571 (1997).

Inoue et al., "Molecular characterization of trhe mde operon involved in L-methionine catabolism of *Pseudomonas putida*", J. Bacteriology, vol. 179, pp. 3956-3962 (1997).

Rinehart et al., "Structures of the Didemnins, Antiviral and Cytotoxic Depsipeptides from a Caribbean Tunicate", Journal of American Chemical Society, vol. 103, pp. 1857-1859 (1981).

(Continued)

*Primary Examiner*—Ponnathapu Achutamurthy
*Assistant Examiner*—Mohammad Meah
(74) *Attorney, Agent, or Firm*—Greenblum & Bernstein, P.L.C.

(57) ABSTRACT

The object of the present invention is to provide a novel dehydrogenase having a property which is different from that of known dehydrogenases. The present invention provides a dehydrogenase having the following physicochemical properties:

(1) effect: to produce N-alkyl-L-alanine from pyruvic acid and alkylamine or dialkylamine using NADPH and/or NADH as coenzyme;

(2) substrate specificity: to show activity to alkylamine or dialkylamine but not to ammonium;

(3) optimal pH when using phenylpyruvic acid and methylamine as substrates is around 10; and (4) when treated at 30 ° C. for 30 minutes, the enzyme is stable at around pH 5 to 10.5.

2 Claims, 7 Drawing Sheets

OTHER PUBLICATIONS

Pettit et al., "Isolation of dolastatins 10-15 from the marine mollusc *Polabella auricularia*", Tetrahedron, vo. 49, No. 41, pp. 9151-9170 (1993).

Dorow et al., "A Novel Preparation of Scalemic N-Methyl-α-amino Acids", Journal of Organic Chemistry, vol. 60, pp. 4986-4987 (1995).

Reddy et al., "A Practical Approach for the Optically Pure N-Methyl-α-amino Acids", Tetrahedron Letters,. vol. 39, pp. 1985-1986 (1998).

Lin et al., "Purification and Characterization of N-Methylalanine Dehydrogenase", The Journal of Biological Chemistry, vol. 250, No. 10, pp. 3746-3751 (1975).

Hanessian et al., "Asymmetric Synthesis of L-Azetidine-2-Carboxylic acid and 3-substituted congeners—Conformationally constrained analogs of Phenylalanine, Naphthylalanine, and Leucine", Bioorganic & Medicinal Chemistry Letters, vol. 9, pp. 1437-1442 (1999).

Fernandez-Garcia et al., "A Short Enantioselective Synthesis of Pipecolic Acid", Tetrahedron: Asymmetry, vol. 6, No. 12, pp. 2905-2906 (1995).

Callens et al., "Preparation of Trans-5-hydroxy-L-Pipecolic acid and Cis-4-Hydroxy-L-Pipecolic acid from L-Baikiain (1,2,5,6-L-Tetrahydropyridine-2-carboxylic acid", Bulletin Society Chim. Belg. vo. 91, No. 8 (1982).

Shiraiwa et al., "Synthesis of Optically Active 1,4-Thiazane-3-carboxylic Acid *via* Optical Resolution by preferential Crystallization of (RS)-2-Amino-3[(2-chloroethyl)sulfanyl]propanoic acid Hydrochloride", Bioscience Biotechnology, Biochemistry, vol. 62, No. 12, pp. 2382-2387 (1998).

Larsson et al., "Synthesis of Amino Acids with Modified Principal Properties 3: Sulfur-containing Amino Acids", Acta Chemica Scandinavica, vol. 48, pp. 517-525 (1994).

Kogami et al., "Synthesis of Optically Active 3-Morpholinecaboxylic Acid and Tetrahydro-2H-1,4-thiazine-3-carboxylic Acid", Bulletin of Chemical Society of Japan, vol. 60, pp. 2963-2965 (1987).

Seebach et al., "Synthesis of Nonproteinogenic (R)- or (S)-Amino acids Analogues of Phenylalanine, Isotopically Labeled and Cyclic Amino Acids from *tert*-Butyl 2-(*tert*-Butyl)-3-methyl-4-oxo-1—imidazolidinecarboxylate (Boc-BMI)", Liebigs Ann. Chemistry, pp. 1215-1232 (1989).

Fujii et al., "Increase in the Rate of L-Pipecolic Acid Production Using *lat*-Expressing *Escherichia coli* by *lysP* and *yeiE* Amplification", Bioscience Biotechnology Biochemistry, vol. 66, No. 9, pp. 1981-1984 (2002).

Kenklies et al., "Proline biosynthesis from L-ornithine in *Clostridium sticklandii*: purification of $\Delta^1$-pyrroline-5-carboxylate reductase, and sequence and expression of the encoding gene, *proC*", Microbiology, vol. 145. pp. 819-826 (1999).

Costilow et al., "Reactions Involved in the Conversion of Ornithine to Proline in Clostridia", Journal of Bacteriology, pp. 662-667 (1969).

Costilow et al., "Ornithine Cyclase (Deaminating)", The Journal of Biological Chemistry, vol. 246, No. 21, pp. 6655-6660 (1971).

Meister et al., "Enzymatic Synthesis of L-Pipecolic acid and L-Proline", Journal of Biological Chemistry, vol. 229, pp. 789-800 (1957).

Payton et al., "$\Delta^1$-Piperideine-2-Carboxylate Reductase of *Pseudomonas putida*" Journal of Bacteriology, vol. 149, No. 3, pp. 864-871 (1982).

Nardini et al., "Purification and characterization of a ketimine-reducing enzyme", European Journal of Biochemistry, vol. 173, pp. 689-694 (1988).

Zoller et al., "Oligonucleotide-directed mutagenesis using M13-derived vectors: an efficient and general procedure for the production of point mutations in any fragment of DNA", Nucleic Acids Research, vol. 10, No. 20, pp. 6487-6500 (1982).

Shortle et al., "Directed Mutagenesis with Sodium Bisulfite", Methods Enzymology, vol. 100, pp. 457-468 (1983).

Reiser et al., "Transfer and Expression of Heterologous Genes in Yeasts Other Than *Saccharomyces cerevisiae*", Advances in Biochemical Engineering, vol. 43, pp. 75-102 (1990).

Miwa et al., "Construction of novel shuttle vectors and a cosmid vector for the glutamic acid-producing bacteria *Brevibacterium lactofermentum* and *Corynebacterium glutamicum*", Gene, vol. 39, pp. 281-286 (1985).

Ozaki et al., "Functional expression of the genes of *Escherichia coli* in gram-positive *Corynebacterium glutamicum*", Molecular & General Genetics, vol. 196, pp. 175-178 (1984).

Heyer et al., "Replicating Plasmids in *Schizosaccharomyces pombe*: Improvement of Symmetric Segregation by a New Genetic Element", Molecular and Cellular Biology, vol. 6, No. 1, pp. 80-89 (1986).

Saunders et al., "Heterologous gene expression in filamentous fungi", Trends in Biotechnology, vol. 7, pp. 283-287 (1989).

Maeda et al., "Production of human α-interferon in silkworm using a baculovirus vector", Nature, vol. 315, pp. 592-597 (1985).

Moore et al., "Culture of Normal Human Leukocytes", The Journal of the American Medical Association, vol. 199, No. 8, pp. 519-524 (1967).

Eagle, "Nutrition Needs of Mammalian Cells in Tissue Culture", Science vol. 122, No. 3168, pp. 501-504 (1955).

Lundholm et al., "Plaque Production by the Polyoma Virus", Virology, vol. 8, p. 396-397 (1959).

Morgan et al., "Nutrition of Animal Cells in Tissue Culture. I. Initial Studies on a Synthetic Medium", Proceeding of the Society for Experimental Biology and Medicine, vol. 73, No. 1, pp. 1-8 (1950).

Geueke et al., "A new bacterial L-amino acid oxidase with a broad substrate specificity: purification and characterization", Enzyme and Microbial Technology, vol. 31, pp. 77-87 (2002).

Lampel et al., "Characterization of the Developmentally Regulated *Bacillus subtilis* Glucose Dehydrogenase Gene", Journal of Bacteriology, vol. 166, No. 1, pp. 238-243 (1986).

Keenan et al., "Synthesis of chiral nonracemic 4-*trans*-substituted pipecolic acid derivatives", Tetrahedron Asymmetry, vol. 10, pp. 4331-4341 (1999).

Letavic et al., "Synthesis and Biological Activity of Selective Pipecolic Acid-Based TNF-αConverting Enzyme (TACE) Inhibitors", Bioorganic & Medicinal Chemistry Letters, vol. 12, pp. 1387-1390 (2002).

Krapcho et al., "Angiotensin-Converting Enzyme Inhibitors. Mercaptan, Caboxyalkyl Dipeptide, and Phosphinic Acid Inhibitors Incorporating 4-Substituted Prolines", Journal of Medical Chemistry, vol. 31, pp. 1148-1160 (1988).

Suzuki et al., "Isolation of Nocotianamine as a Gelatinase Inhibitor", The Journal of Antibiotics, vol. 49,. pp. 1284-1285 (1996).

Sutton et al., "Synthesis and SAR of 4-Carboxy-2-azetidinone Mechanism-Based Tryptase Inhibitors", Bioorganic & Medicinal Chemistry Letters, vol. 12, pp. 3229-3233 (2002). Romanos et al., "Foreign Gene Expression in Yeast : a Review", Yeast, vol. 8, pp. 423-488, (1992).

English Language Abstract of JP57-183799 filed Nov. 12, 1982.

Mass spectrum of each peak of methionine

DEHYDROGENASE AND A GENE ENCODING THE SAME

This application is a continuation in part of application PCT/JP03/02204 filed Feb. 27, 2003, which was published in Japanese under PCT Article 21(2) on Apr. 9, 2003, which claims the benefit of foreign application Japan JP2002-054198 filed Feb. 28, 2002.

TECHNICAL FIELD

The present invention relates to a novel dehydrogenase, a DNA encoding the same, and a method of producing N-alkyl amino acids using the same. Among N-alkyl amino acids, N-methyl amino acids in particular are known to exist as a part of a structure of naturally occurring physiologically active substances such as Didemnin or dolastatin (J. Am. Chem. Soc. 1981, 103, p 1857–1859; Tetrahedron 1993, 49, p 9151–9170). These are useful substances which have recently attracted attention as intermediate materials for medicaments or agricultural chemicals. In addition, the present invention relates to a method of producing optically active cyclic amino acids which are useful industrially.

BACKGROUND ART

Chemical reactions such as reductive alkylation of azides (J. Org. Chem. 1995, 60, p 4986–4987) or reductive ring-opening reaction of oxazolidine derivatives (Tetrahedron Letter 39 (1998) 1985–1986) and the like have been known for the production of N-substituted amino acids.

Although microbiological methods for producing amino acids from 2-oxocarboxylic acid derivatives using a dehydrogenase or aminotransferase are known, these methods mainly include simple amination. The known methods using a substituted amino group are only a simple methylamination method such as the method of producing N-methylalanine from pyruvic acid using microorganisms of genus *Pseudomonas* (J. Biol. Chem., 250, p 3746–3751 (1975)) and the methylamination method using microorganisms of genus *Rhodococcus* and *Arthrobacter* (JP Patent Publication (Kokai) No. 2001–190298).

With respect to enzymes involved in the above reaction, it is reported in J. Biol. Chem., 250, p 3746–3751 (1975) that N-methylalanine dehydrogenase from *Pseudomonas* MS ATCC 25262 was purified.

On the other hand, as for a method of producing cyclic amino acid chemically, such methods have been known as producing L-azetidine-2-carboxylic acid (Stephen Hanessian et al., Bioorganic & Medicinal Chemistry Letters (1999) vol. 9, pp. 1437–1442, and U.S. Pat. No. 5,942,630); pipecolic acid (Concepcion F Garcia et al., Tetrahydron Asymmetry (1995) vol. 6, pp. 2905–2906); 4- and 5-hydroxypipecolic acid (Roland E. A. Callens, et al, Bull. Soc. Chim. Belg. vol. 91, (1982) pp 713–723); 1,4-thiazane-3-carboxylic acid (Biosci. Biotechnol. Biochem., vol. 62, pp 2382–2387 T Shiraiwa, et al.)(Acta Chemica Scandinavica, 1994, vol. 48, pp 517–525, U Larsson et al.); L-3-morpholine carboxylic acid (Bull. Chem. Soc. Jpn., vol. 60, pp 2963–2965, 1987, Y Kogami et al.); (S)-azepane-2-carboxylic acid (Liebigs. Ann. Chem. 1989, pp 1215–1232, D. Seebach et al.); and the like.

As for a method of producing cyclic amino acid biochemically, such methods have been known as producing L-pipecolic acid from L-lysine while utilizing pyrroline-5-carboxylate reductase (EC 1.5.1.2) (Tadashi Fujii et al., Bioscience Biotechnology Biochem (2002) vol.66, pp. 1981–1984); L-proline from L-ornithine while utilizing pyrroline-5-carboxylate reductase (EC 1.5.1.2) (Janet Kenklies et al., Microbiology (1999), vol.145, pp. 819–826; and Ralph N Costilow et al., Journal of Bacteriology (1969) vol.100, pp. 662); L-proline from L-ornithine with ornithine cyclodeaminase (Ralph N Costilow et al., Journal of Biological Chemistry (1971) vol.246, pp. 6655–6660); various types of cyclic amino acids from various types of diamino acids with ornithine cyclodeaminase (International Publication WO 02/101003); and the like.

On the other hand, as for an enzyme that reduces a cyclic amino acid having a double bond at 1-site, pyrroline-2-carboxylate reductase: EC1.5.1.1, for example, derived from animal or fungus is known as the enzyme that reduces Δ-1-pyrroline-2-carboxylic acid and Δ-1-piperidine-2-carboxylic acid to generate proline and pipecolic acid respectively (Alton Meister et al., Journal of Biological Chemistry (1957) vol. 229, pp. 789–800).

Further, there is a report that describes such metabolism of a bacterium belonging to *Pseudomonas* species as generating L-pipecolic acid from D-lysine through Δ-1-piperidine-2-carboxylic acid as an intermediate, and that piperideine-2-carboxylate reductase: EC 1.5.1.21 conducts the reduction reaction in the reactions (Cecil W Payton et al., Journal of Bacteriology (1982) vol. 149, pp. 864–871).

In addition, it has been found that ketimine-reducing enzyme: EC 1.5.1.25 derived from liver of porcine reduces S-aminoethylcysteine ketimine, lanthionine ketimine and cystathionine ketimine (Mirella Nardini et al., European Journal of Biochemistry (1988) vol.173, pp. 689–694).

However, the method reported by Fujii et al. (Tadashi Fujii et al., Bioscience Biotechnology Biochem (2002) vol.66, pp. 1981–1984) includes steps of using L-lysine 6-aminotransferase for L-lysine to generate Δ-1-piperidine-6-carboxylic acid as the intermediate, and further acting the reductase on it to give L-pipecolic acid. The method can deal with only the case where the starting material is L-lysine, and can not be applied to the production of other cyclic amino acids.

The report of Costilow et al. (Ralph N Costilow et al., Journal of Biological Chemistry (1971) vol.246, pp. 6655–6660) describes the step of obtaining L-proline by using Omithine Cyclase for L-ornithine, but also does not describe any products other than proline. Denis et al. (WO 02/101003) disclose a method of obtaining L-pipecolic acid, L-Thiomorpholine-2-carboxylic acid, 5-hydroxy-L-pipecolic acid and the like by using Ornithine Cyclase, but do not describe yield, optical purity and the like.

In any of the aforementioned methods, the optical purity of the produced cyclic amino acid depends on the optical purity of a starting amino acid, and an optically active cyclic amino acid can not be obtained from a starting material of whole racemic body with a high yield.

On the other hand, a method employing a cyclic amino acid having a double bond at 1-site as an intermediate is advantageous industrially, because it can use racemic cyclic amino acids or diamino acids.

Enzyme reactions that deal with L-proline and L-pipecolic acid, L-Thiomorphine and the like, respectively, are confirmed. However, in each case, an enzyme reaction is confirmed only biochemically, and no example of industrial production has been known. Further, there is such a description that enzymes derived from animal are very unstable, making practical application difficult by using these enzymes.

DISCLOSURE OF THE INVENTION

However, as stated above, known amino acid dehydrogenases and N-methyl amino acid dehydrogenases have limited substrate specificity, for example, to amines or dicarbonyl group-containing compounds, and its applicable range is narrow. In addition, N-methylamination using the above known enzymes is not industrially advantageous because normal amino acids having no amino group substituent are produced simultaneously in addition to N-methyl-amino acids. For these reasons, it has been desired to obtain a novel dehydrogenase. In other words, an object of the present invention is to provide a novel dehydrogenase having a property which is different from that of known dehydrogenases.

Further, it is thought that optically active cyclic amino acids can be produced industrially and inexpensively at a high yield by isolating an enzyme that is enzymatically stable, reduces cyclic amino acids having a double bond at 1-site and reacts widely on various types of substrate, and by using an immobilized enzyme thereof or a recombinant microorganism where a gene of the enzyme was introduced. Accordingly, an object of the present invention is to provide a method of producing various types of optically active cyclic amino acids industrially and inexpensively by obtaining a cyclic amino acid having a double bond at 1-site as an intermediate from industrially inexpensive diamino acid or racemic cyclic amino acids, and by using an enzyme that reduces the same.

As a result of extensive investigation to solve the above object, the present inventors have succeeded in isolating a novel dehydrogenase from *Pseudomonas putida* ATCC 12633 strain, thus coming to complete the invention.

Further, the present inventors found that N-methyl-L-amino acid dehydrogenase reduces cyclic amino acids having a double bond at 1-site to generate optically active cyclic amino acids efficiently. Further, cyclic amino acids having a double bond at 1-site may be produced efficiently from racemic cyclic amino acids or diamino acid by using a corresponding known enzyme, or may be obtained chemically. Accordingly, by a combination of the reaction for the generation of the cyclic amino acid having a double bond at 1-site and the stereoselective reduction reaction, inexpensive optically active cyclic amino acids can be produced industrially.

The present invention has been achieved on the basis of these findings.

Thus, the present invention provides a dehydrogenase having the following physicochemical properties:

(1) effect: to produce N-alkyl-L-alanine from pyruvic acid and alkylamine or dialkylamine using NADPH and/or NADH as coenzyme;

(2) substrate specificity: to show activity to alkylamine or dialkylamine but not to ammonium;

(3) optimal pH when using phenylpyruvic acid and methylamine as substrates is around 10; and (4) when treated at 30° C. for 30 minutes, the enzyme is stable at around pH 5 to 10.5.

Another aspect of the present invention provides any one of the following polypeptides:

(1) a polypeptide having an amino acid sequence represented by SEQ ID No. 1;

(2) a polypeptide having an amino acid sequence wherein one or more amino acids are deleted, substituted and/or added in the amino acid sequence represented by SEQ ID No. 1, and having dehydrogenase activity; or (3) a polypeptide having an amino acid sequence which shows 50% or more homology to the amino acid sequence represented by SEQ ID No. 1, and having dehydrogenase activity.

Yet another aspect of the invention provides a DNA encoding the polypeptide of the present invention.

Yet another aspect of the invention provides any one of the following DNAs:

(1) a DNA having a nucleotide sequence represented by SEQ ID No. 2;

(2) a DNA having a nucleotide sequence wherein one or more nucleotides are deleted, substituted and/or added in the nuclotide sequence represented by SEQ ID No. 2, and encoding a polypeptide having dehydrogenase activity; or (3) a DNA which hybridizes under stringent conditions to a DNA having the nucleotide sequence represented by SEQ ID No. 2, and encodes a polypeptide having dehydrogenase activity.

Yet another aspect of the invention provides a recombinant vector carrying the DNA of the present invention as mentioned above.

Yet another aspect of the invention provides a transformant containing the DNA or recombinant vector of the present invention as mentioned above.

Yet another aspect of the invention provides a method of producing N-alkyl-amino acid derivatives, which comprises a step of reacting a dicarbonyl group-containing compound represented by the following formula (I):

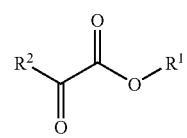

(I)

wherein $R^1$ represents a hydrogen atom or an alkyl group which may be substituted, and $R^2$ represents an alkyl group which may be substituted or an aryl group which may be substituted;

with an alkyl-substituted amine represented by $R^3(R^4)NH$ wherein $R^3$ and $R^4$ each independently represents a hydrogen atom or an alkyl group which may be substituted, provided that both $R^3$ and $R^4$ are not hydrogen atoms at the same time;

in the presence of the dehydrogenase, polypeptide or transformant of the present invention.

$R^1$ is preferably a hydrogen atom.

$R^3$ is preferably a straight, branched or cyclic $C_{1-6}$ alkyl group which may be substituted with an amino group, and $R^4$ is preferably a hydrogen atom.

The compound represented by formula (I) is preferably pyruvic acid, phenylpyruvic acid, β-fluoropyruvic acid, 2-oxobutyric acid, 2-ketohexanoic acid, or 2-keto n-valeric acid.

Yet another aspect of the invention provides a method of producing N-alkyl-amino acid derivatives, which comprises a step of reacting aminocarboxylic acids represented by the following formula (II):

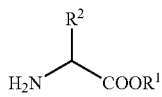
(II)

wherein R¹ represents a hydrogen atom or an alkyl group which may be substituted, and R² represents an alkyl group which may be substituted or an aryl group which may be substituted;

an enzyme capable of converting aminocarboxylic acids represented by the formula (II) to compounds represented by the formula (I):

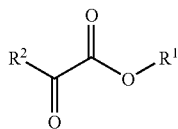
(I)

wherein R¹ and R² are the same as defined in the formula (II)); and an alkyl-substituted amine represented by R³(R⁴)NH wherein R³ and R⁴ each independently represent a hydrogen atom or an alkyl group which may be substituted, provided that both R³ and R⁴ are not hydrogen atoms at the same time;

in the presence of the dehydrogenase, polypeptide or transformant of the present invention.

R³ is preferably a straight, branched or cyclic $C_{1-6}$ alkyl group which may be substituted with amino group, and R⁴ is preferably a hydrogen atom.

The aminocarboxylic acid represented by the formula (II) is preferably phenylalanine or methionine.

The enzyme capable of converting aminocarboxylic acids represented by the formula (II) to alkyl-substituted amines represented by the formula (I) is preferably D-amino acid oxidase, L-amino acid oxidase, D-amino acid dehydrogenase, L-amino acid dehydrogenase, or amino acid transferase.

Yet another aspect of the invention provides a method of producing L-cyclic amino acid, which comprises a step of allowing N-methyl-L-amino acid dehydrogenase or a cell containing the same, a preparation of the cell, or a culture solution obtained by culturing the cell to act on a cyclic amino acid having a double bond at 1-site represented by the following formula (I):

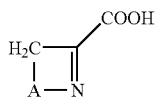
(I)

wherein A represent an alkyl chain having a chain length of 1 to 6 atoms, which may includes at least one type of hetero atom selected from the group consisting of a sulfur atom, an oxygen atom and a nitrogen atom in the chain or at the terminal thereof, and may be substituted, so as to generate an L-cyclic amino acid represented by the following formula (II):

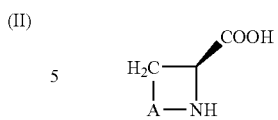
(II)

wherein A represents the same meaning as described above.

Preferably, the N-methyl-L-amino acid dehydrogenase is a polypeptide represented by the following (A), (B) or (C):

(A) a polypeptide having an amino acid sequence represented by SEQ ID No. 1;

(B) a polypeptide having an amino acid sequence wherein one or more amino acids are deleted, substituted and/or added in the amino acid sequence represented by SEQ ID No. 1, and having N-methyl-L-amino acid dehydrogenase activity; or (C) a polypeptide having an amino acid sequence which shows 50% or more homology to the amino acid sequence represented by SEQ ID No. 1, and having N-methyl-L-amino acid dehydrogenase activity.

Preferably, the N-methyl-L-amino acid dehydrogenase is N-methyl-L-amino acid dehydrogenase having the following physicochemical properties:

(1) effect: to produce N-alkyl-L-alanine from pyruvic acid and alkylamine or dialkylamine using NADPH and/or NADH as coenzyme;

(2) substrate specificity: to show activity to alkylamine or dialkylamine but not to ammonium;

(3) optimal pH when using phenylpyruvic acid and methylamine as substrates is around 10; and (4) when treated at 30° C. for 30 minutes, the enzyme is stable at around pH 5 to 10.5.

Preferably, the cell containing N-methyl-L-amino acid dehydrogenase is a cell transformed with DNA encoding N-methyl-L-amino acid dehydrogenase.

Preferably, the DNA encoding N-methyl-L-amino acid dehydrogenase is a DNA encoding a protein represented by the following (A), (B) or (C):

(A) a protein having an amino acid sequence represented by SEQ ID No. 1;

(B) a protein having an amino acid sequence which shows 50% or more homology to the amino acid sequence represented by SEQ ID No. 1, and having N-methyl-L-amino acid dehydrogenase activity; or (C) a protein comprising an amino acid sequence wherein one or more amino acids are deleted, substituted and/or added in the amino acid sequence represented by SEQ ID No. 1, and having N-methyl-L-amino acid dehydrogenase activity.

Preferably, the DNA encoding N-methyl-L-amino acid dehydrogenase is a DNA shown by the following (D), (E) or (F):

(D) a DNA having a nucleotide sequence represented by SEQ ID No. 2;

(E) a DNA which hybridizes under stringent conditions to a DNA having the nucleotide sequence represented by SEQ ID No. 2 or a complementary sequence thereof, and encodes a protein having N-methyl-L-amino acid dehydrogenase activity; or (F) a DNA having a nucleotide sequence wherein one or more nucleotides are deleted, substituted and/or added in the nucleotide sequence represented by SEQ ID No. 2, or complementary sequence thereof, and encoding a protein having N-methyl-L-amino acid dehydrogenase activity.

Preferably, A is a linear alkyl chain having 1 to 5 carbons in the compound represented by the aforementioned formulae (I) and (II).

Preferably, A is an alkyl chain containing an hetero atom which is selected from the group consisting of —CHOHCH$_2$—, —CH$_2$CHOHCH$_2$—, —SCH$_2$—, —SC$_2$H$_4$—, —SC$_3$H$_6$13 , —OCH$_2$—, —OC$_2$H$_4$—, —OC$_3$H$_6$—, —NHCH$_2$—, —NHC$_2$H$_4$—, —NHC$_3$H$_6$—, —NHCH$_2$CHCOOH—, —C$_2$H$_4$NHCO—, —C$_2$H$_4$NHCN—, —C$_2$H$_4$CHCOOH—, —SCH$_2$CHCOOH—, —SC$_2$H$_4$CHCOOH—, —C$_3$H$_6$NHCH$_2$CHCOOH—, —NHCHCOOHCH$_2$— and —CH$_2$NHCHCOOHC$_2$H$_4$— in the compound represented by the aforementioned formulae (I) and (II).

Preferably, A is an alkyl chain containing a hetero atom which is selected from the group consisting of a linear alkyl chain having 2 to 4 carbons (—C$_2$H$_4$—, C$_3$H$_6$—, —C$_4$H$_8$—), —CHOHCH$_2$—, —C$_2$H$_4$CHOHCH$_2$—, —SCH$_2$—, —SC$_2$H$_4$—, —SC$_3$H$_6$— and —OC$_2$H$_4$— in the compound represented by the aforementioned formulae (I) and (II).

Yet another aspect of the invention provides a method of producing L-cyclic amino acids which comprises steps of allowing an enzyme capable of converting an amino group at α-site of diamino acid into a keto group to generate α-keto acid to act on a chained α,ω-diamino acid represented by the following formula (III):

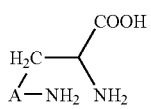

(III)

wherein A represents the same meaning as described above, to generate a cyclic amino acid having a double bond at 1-site represented by the following formula (I):

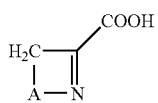

(I)

wherein A represents the same meaning as described above; and generating an L-cyclic amino acid represented by the following formula (II):

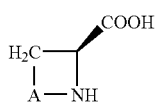

(II)

wherein A represents the same meaning as described above, from the above-obtained cyclic amino acid having a double bond at 1-site by the aforementioned method.

Preferably, the enzyme capable of converting an amino group at α-site of diamino acid into a keto group to generate α-keto acid is an enzyme selected from the group consisting of D-amino acid oxydase, L-amino acid oxydase, D-amino acid dehydrogenase, L-amino acid dehydrogenase, D-amino acid transferase and L-amino acid transferase.

Yet another aspect of the invention provides a method of producing L-cyclic amino acids which comprises steps of allowing an enzyme capable of oxidizing an amino group at 1-site to act on a cyclic amino acid represented by the following formula (IV):

(IV)

wherein A represents the same meaning as described above, to generate a cyclic amino acid having a double bond at 1-site represented by the following formula (I):

(I)

wherein A represents the same meaning as described above; and generating an L-cyclic amino acid represented by the following formula (II):

(II)

wherein A represents the same meaning as described above, from the above-obtained cyclic amino acid having a double bond at 1-site by the aforementioned method.

Preferably, the enzyme capable of oxidizing an amino group at 1-site of cyclic amino acid to generate a cyclic amino acid having a double bond at 1-site is an enzyme selected from the group consisting of D-amino acid oxydase, D-amino acid dehydrogenase and D-amino acid transferase.

Yet another aspect of the invention provides a cyclic amino acid, [1,4]thiazepane-3-carboxylic acid:

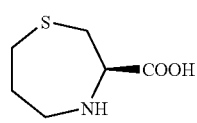

[1,4]tiazepane-3-carboxylic acid

BEST MODE FOR CARRYING OUT THE INVENTION

Figure 1:
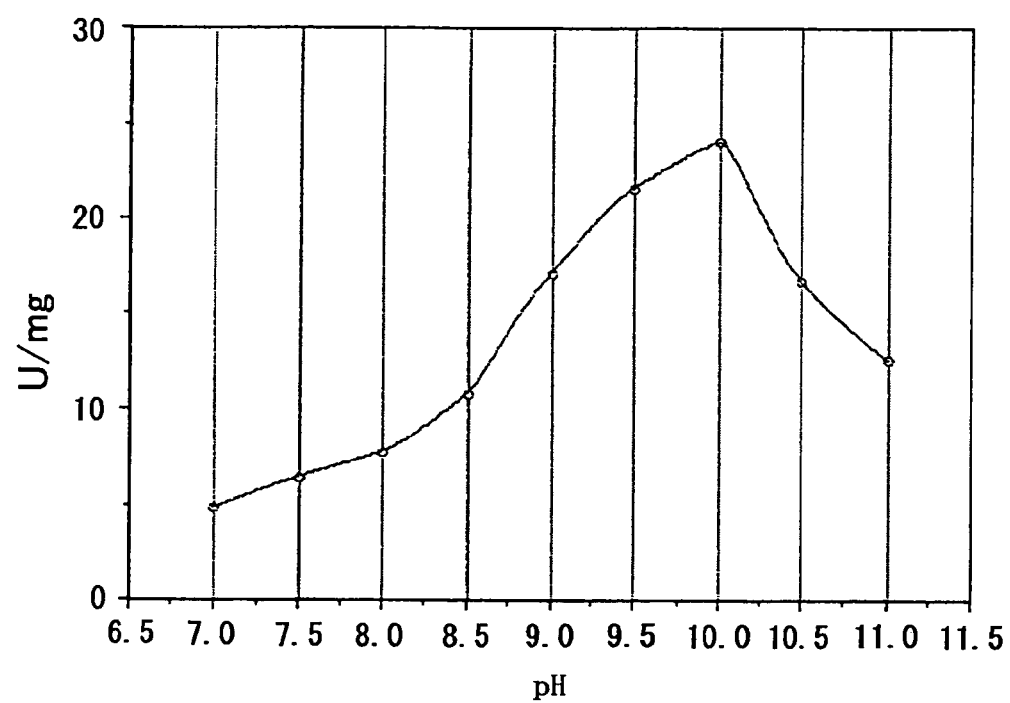
FIG. 1 is a graph showing the optimal pH for the N-methyl-L-phenylalanine dehydrogenase of the present invention.

The embodiments of the present invention will be described in detail below.

(I) Dehydrogenase and Polypeptide of the Present Invention

The dehydrogenase of the present invention has the following physicochemical properties:

(1) effect: To produce N-alkyl-L-alanine from pyruvic acid and alkylamine or dialkylamine using NADPH and/or NADH as coenzyme;

(2) substrate specificity: To show activity to alkylamine or dialkylamine but not to ammonium;

(3) optimal pH when using phenylpyruvic acid and methylamine as substrates is around 10; and, (4) when treated at 30° C. for 30 minutes, the enzyme is stable at around pH 5 to 10.5.

The dehydrogenase of the present invention can be obtained, for example, by screening using ammonium, alkylamine and dialkylamine in the presence of a dicarbonyl group-containing compound such as phenylpyruvic acid, and NADPH and/or NADH.

In screening, proliferated cells from cultures of microorganisms having dehydrogenase activity, sonicated products of the cells, or a crude enzyme or purified enzyme isolated from the same by conventional procedures, can be used.

In addition, the feature of the dehydrogenase of the present invention is that the enzyme is stable at pH around 5 to 10.5, with the optimal pH at around 10.

The dehydrogenase can be isolated from, for example, microorganisms belonging *Pseudomonas putida*, particularly preferably *Pseudomonas putida* ATCC 12633 strain.

Specific examples of the above mentioned dehydrogenase include polypeptide represented by the amino acid sequence of SEQ ID No. 1, and homologues thereof having dehydrogenase activity.

The dehydrogenase represented by the amino acid sequence of SEQ ID No. 1 has the following properties in addition to the properties shown in (1) to (4) above:

(5) molecular weight as measured by gel filtration analysis using Superose 12HR10/30 (Amersham Biosciences) is approximately 80 to 93 kiloDaltons, and a polypeptide band estimated to be at least approximately 36 kiloDaltons is shown in SDS-polyacrylamide electrophoresis;

(6) the optimal temperature determined by the measurement of activity using phenylpyruvic acid and methylamine as substrates is around 35° C.;

(7) thermal stability is shown at temperatures less than approximately 30° C., when treated at the optimal pH (pH 10 when using phenylpyruvic acid and methylamine as substrates) for 30 minutes;

(8) to show activity towards pyruvic acid as well as at least to 2-ketohexanoic acid, phenylpyruvic acid, 2-oxobutyric acid, β-fluoropyruvic acid, and 2-keto n-valeric acid;

(9) activity is inhibited by divalent heavy metals, such as 0.01 mM mercury chloride ($HgCl_2$) and 0.01 mM copper chloride ($CuCl_2$).

The homologues of the dehydrogenase of the present invention include:

a polypeptide having an amino acid sequence wherein one or more (preferably 1 to 20, more preferably 1 to 15, even more preferably 1 to 10, even more preferably 1 to 7, most preferably approximately 1 to 5) amino acids are deleted, substituted and/or added in the amino acid sequence represented by SEQ ID No. 1, and having dehydrogenase activity; or a polypeptide showing 50% or more, preferably 60% or more, more preferably 70% or more, more preferably 80% or more, even more preferably 90% or more, even more preferably 95% or more, most preferably 97% or more homology to the amino acid sequence represented by SEQ ID No. 1, and having dehydrogenase activity.

Homology search of the polypeptides can be performed, for example, by using FASTA program and BLAST program on DNA Databank of JAPAN (DDBJ).

Dehydrogenase activity is generally a collective term for activity that catalyzes dehydrogenation reaction. In the present invention, it is used to mean an activity with which carbonyl compounds are alkylaminated by alkyl amines and coenzymes involved in a redox reaction such as NADH or NADPH.

The dehydrogenase of the present invention can be obtained by isolation/purification from cultures of microorganisms having dehydrogenase activity as stated above, as well as by isolating a DNA encoding the reductase from any microorganism having dehydrogenase activity by using a probe constructed based on a nucleotide sequence encoding a portion or all of amino acid sequence of the present invention and subjecting it to a genetic engineering, as described below.

Alternatively, the dehydrogenase of the present invention can also be produced by chemical synthesis methods, such as Fmoc (Fluorenylmethyloxy carbonyl) method and tBoc (t-butyloxycarbonyl) method. The dehydrogenase of the present invention may also be chemically synthesized using peptide synthesizers manufactured by, such as Sowa Trading Co., Inc. (Advanced Chem Tech, Inc., USA), PerkinElmer Japan Co., Ltd. (Perkin-Elmer Corp., USA), Amersham Pharmacia Biotech, Inc., Aloka, Co., Ltd. (Protein Technology Instrument, USA), Kurabo Industries Ltd. (Synthecell-Vega, USA), Japan PerSeptive Biosystems Ltd. (PerSeptive, USA), and Shimadzu Corporation.

(II) DNA of the Present Invention

According to the present invention, a DNA encoding the above dehydrogenase or homologues thereof is provided.

Examples of a DNA encoding the above dehydrogenase include those containing the nucleotide sequence represented by SEQ ID No. 2.

Examples of homologues of DNA encoding dehydrogenase of the present invention include:

a DNA having the nucleotide sequence wherein one or more (preferably 1 to 60, more preferably 1 to 30, even more preferably 1 to 20, even more preferably 1 to 10, most preferably approximately 1 to 5) nucleotides are deleted, substituted and/or added in the nucleotide sequence represented by SEQ ID No. 2, and encoding a polypeptide having dehydrogenase activity; or a DNA which hybridizes under stringent conditions to a DNA having the nucleotide sequence represented by SEQ ID No. 2, and encoding a polypeptide having dehydrogenase activity.

One having ordinary skill in the art would be able to obtain the desired homologues by introducing appropriate substitution, deletion, insertion and/or addition mutations into the DNA of SEQ ID No. 2 by using methods such as site-directed mutagenesis (Nucleic Acid Res. 10, pp. 6487 (1982); Methods in Enzymol. 100, pp. 448 (1983); Molecular Cloning 2nd Edt., Cold Spring Harbor Laboratory Press (1989) (hereinafter referred to as "Molecular Cloning 2nd ed."); PCR A Practical Approach, IRL Press pp. 200 (1991)).

The term "DNA which hybridizes under stringent conditions" is used herein to mean the nucleotide sequence of DNA which can be obtained by methods such as colony hybridization, plaque hybridization, or southern blot hybridization using a DNA as probes. This includes, for example, DNA which can be identified by hybridization in the presence of 0.7 to 1.0 M NaCl at 65° C. using a filter on which DNA or DNA fragments from a colony or plaque is immobilized, followed by washing of the filter with 0.1 to 2×SSC solution (composition of 1×SSC is 150 mM sodium chloride and 15 mM sodium citrate) at 65° C.

Hybridization can be carried out according to methods such as those described in "Molecular Cloning 2nd ed."

Examples of homologues of the above DNA include those showing 60% or more, preferably 70% or more, more preferably 80% or more, most preferably 90% or more homology to the nucleotide sequence of SEQ ID No. 2.

A DNA encoding the dehydrogenase of the present invention can be isolated, for example, by the following method.

First, the dehydrogenase of the present invention is purified, and then the N-terminal amino acid sequence is analyzed. Then, ordinary genetic engineering analysis methods such as PCR cloning can be utilized to isolate a gene encoding a dehydrogenase of interest from chromosomal DNA, and its nucleotide sequence can be analyzed. Since the nucleotide sequence was determined in the present invention, it will also be possible to construct primers based on the nucleotide sequence to clone the gene of interest, or the gene of interest can also be synthesized using a DNA synthesizer.

(III) Recombinant Vector and Transformant of the Present Invention

A DNA encoding the dehydrogenase of the present invention obtained in above (II) can be inserted into a well-known expression vector to provide a dehydrogenase expression vector. In addition, by cultivating a transformant transformed with this expression vector, a dehydrogenase can be obtained from the transformant.

Examples of microorganisms subjected to transformation for expression of the dehydrogenase of the present invention are not particularly limited, as long as the host itself does not have an adverse effect on the present reaction. Specific examples include the following microorganisms:

Bacteria of which a host vector system is developed, such as genus *Escherichia*, genus *Bacillus*, genus *Pseudomonas*, genus *Serratia*, genus *Brevibacterium*, genus *Corynebacterium*, genus *Streptococcus*, and genus *Lactobacillus*;

Mycobacteria of which a host vector system is developed, such as genus *Rhodococcus* and genus *Streptomyces*;

Yeasts of which a host vector system is developed, such as genus *Saccharomyces*, genus *Kluyveromyces*, genus *Schizosaccharomyces*, genus *Zygosaccharomyces*, genus *Yarrowia*, genus *Trichosporon*, genus *Rhodosporidium*, genus *Hansenula*, genus *Pichia*, and genus *Candida*;

Fungi of which a host vector system is developed, such as genus *Neurospora*, genus *Aspergillus*, genus *Cephalosporium*, and genus *Trichoderma*.

Among the above microorganisms, preferably genus *Escherichia*, genus *Bacillus*, genus *Brevibacterium*, and genus *Corynebacterium*, most preferably genus *Escherichia* and genus *Corynebacterium* are used as hosts.

The process for preparing transformants and the construction of recombinant vectors compatible with the host can be accomplished according to conventional technology used in the fields of molecular biology, bioengineering, and genetic engineering (see for example "Molecular Cloning 2nd ed.").

In particular, it is necessary to introduce the DNA of the present invention into a plasmid or a phage vector that exists stably within microorganisms, or to introduce the DNA of the present invention directly into a host genome to allow for transcription/translation of its genetic information.

It is preferred to incorporate a promoter 5'-upstream to the DNA of the present invention, more preferably to incorporate a terminator 3'-downstream, respectively. Promoters and terminators which can be used in the present invention are not particularly limited, provided that they are promoters and terminators known to function within the microorganism employed as a host. Vectors, promoters and terminators which can be utilized in each of the microorganisms are described in detail in, for example, "Basic Course in Microbiology 8: Genetic Engineering (Biseibutugaku Kisokouza 8 Idennsikougaku)", Kyoritsu Shuppan Co., Ltd., and especially for yeasts in Adv. Biochem. Eng. 43, 75–102 (1990) and Yeast 8, 423–488 (1992).

Specifically, when using, for example, microorganisms of genus *Escherichia*, in particular *Escherichia coli*, examples of plasmid vectors include pBR and pUC plasmids, and there is used promoters derived from, for example, lac (β-galactosidase), trp (tryptophan operon), tac, trc (fusion of lac and trp), and λ phage pL and PR. Examples of terminators include terminators derived from trpA, phage, and rrnB ribosomal RNA.

When using microorganisms of genus *Bacillus*, vectors include pUB110 and pC194 plasmids. Integration into chromosomes is also possible. Promoters and terminators of enzyme genes such as alkaline protease, neutral protease, and α-amylase, can be utilized as promoter and terminator.

When using microorganisms of genus *Pseudomonas*, vectors include common host vector systems which have been developed for, for example, *Pseudomonas putida* and *Pseudomonas cepacia*, and amphotropic vector pKT240 (comprising genes required for autonomous replication, such as those derived from RSF1010) which is based on TOL plasmid associated with degradation of toluene compounds.

When using microorganisms of genus *Brevibacterium*, in particular *Brevibacterium lactofermentum*, vectors include plasmid vectors such as pAJ43 (Gene 39, 281 (1985)). Various promoters and terminators used in *Escherichia coli* can be utilized as promoter and terminator.

When using microorganisms of genus *Corynebacterium*, in particular *Corynebacterium glutamicum*, vectors include plasmid vectors such as pCS11 (JP Patent Publication (Kokai) No. 57-183799) and pCB101 (Mol. Gen. Genet. 196, 175 (1984).

When using microorganisms of genus *Saccharomyces*, in particular *Saccharomyces cerevisiae*, vectors include YRp, YEp, YCp, and YIp plasmids. Promoters and terminators of various enzyme genes such as alcohol dehydrogenase, glyceraldehyde-3-phosphate dehydrogenase, acid phosphatase, β-galactosidase, phosphoglycerate kinase, and enolase can also be utilized as promoter and terminator.

When using microorganisms of genus *Schizosaccharomyces*, vectors include plasmid vector derived from *Schizosaccharomyces pombe* as described in Mol. Cell. Biol. 6, 80 (1986). In particular, pAUR224 is commercially available from Takara Shuzo Co. Ltd. and can be easily utilized.

When using microorganisms of genus *Aspergillus*, *Aspergillus niger* and *Aspergillus oryzae* are among the most investigated fungi, and integration into plasmids or chromosomes can be employed. Promoters from extracellular protease or amylase can be utilized (Trends in Biotechnology 7, 283–287 (1989)).

Other host vector systems corresponding to various microorganisms have been developed, and they can be used as appropriate.

Other than microorganisms, various host vector systems have been developed in plants and animals. In particular, systems expressing large amounts of heterologous protein in insects using silkworms (Nature 315, 592–594 (1985)) or plants such as rapeseed, corn, and potato, and systems using cell-free extract of *Escherichia coli* or cell-free synthetic pathways such as of wheat germ have been developed, and they can be suitably used.

A transformant carrying the DNA of the present invention can be cultured, and the dehydrogenase of the present invention can be isolated and purified from the culture using known methods.

Cultivation of a transformant carrying the DNA of the present invention can be accomplished by ordinary methods used in cultivation of hosts.

When the transformants of the invention are prokaryotes such as *Escherichia coli* or eukaryotes such as yeasts, the medium for cultivating these microorganisms may be either natural or synthetic medium containing carbon sources which can be assimilated by the microorganisms, nitrogen sources, inorganic salts and the like, provided that the medium is capable of efficient cultivation of transformants. Cultivation is preferably carried out under aerobic conditions such as by shaking culture or deep aeration stirring culture. Cultivation temperature is generally in the range of 15 to 40° C., and cultivation time is generally in the range of 16 hours to 7 days. During cultivation, pH is maintained at 3.0 to 9.0. pH is adjusted with, for example, an inorganic or organic acid, alkaline solution, urea, calcium carbonate, or ammonium. Antibiotics, such as ampicillin or tetracycline, may be supplemented to the medium during cultivation, as required.

Examples of mediums for culturing transformants obtained using animal cells as hosts include commonly used RPM11640 medium [The Journal of the American Medical Association, 199, 519 (1967)], Eagle's MEM medium [Science, 122, 501 (1952)], DMEM medium [Virology, 8, 396 (1959)], 199 medium [Proceeding of the Society for the Biological Medicine, 73, 1 (1950)], and the above mediums to which fetal bovine serum has been supplemented. Cultivation is generally carried out for 1 to 7 days under conditions, such as at pH 6 to 8, 30 to 40° C., in the presence of 5% $CO_2$. Antibiotics, such as kanamycin or penicillin, may be supplemented to the medium during cultivation, as required.

Ordinary methods of protein isolation and purification may be used to isolate and purify the dehydrogenase of the present invention from cultures of transformants.

For example, when the dehydrogenase of the present invention is expressed within cells in a dissolved state, cells can be collected by centrifugation after cultivation, suspended in aqueous buffer, and disrupted by for example ultrasonicator, french press, Manton Gaulin homogenizer or Dynomill, to obtain a cell-free extract. Supernatant obtained by centrifugation of the cell-free extract is subjected to ordinary methods of protein isolation and purification, i.e. solvent extraction, salt precipitation with ammonium sulfate or the like, desalination, precipitation with organic solvents or the like, diethylaminoethyl (DEAE) sepharose, anion exchange chromatography using resins such as DIAION HPA-75 (Mitsubishi Chemical Corporation), cation exchange chromatography using resins such as S-Sepharose FF (Pharmacia), hydrophobic chromatography using resins such as butyl sepharose and phenyl sepharose, gel filtration using molecular sieves, affinity chromatography, chromatofocusing, and electrophoresis such as isoelectric focusing, alone or in combination, to obtain purified sample.

In case where the dehydrogenase of the present invention is expressed within cells in the form of insoluble matter, cells can similarly be disrupted after collection, and precipitated fraction can be obtained by centrifugation. Then, the dehydrogenase is collected by ordinary methods. The insoluble matter of the dehydrogenase is then solubilized with a protein denaturing agent. The solubilized solution can then be diluted in or dialyzed against solution which either does not contain a protein denaturing agent or the concentration of a protein denaturing agent is protein is low enough not to denature dehydrogenase, to configure the dehydrogenase in its proper structure, and then the dehydrogenase can be isolated and purified as above to obtain purified sample.

(IV) Production of N-alkyl-amino Acid Derivatives with the Dehydrogenase of the Invention The present invention further relates to a method of producing an N-alkyl-amino acid derivative, which comprises a step of reacting dicarbonyl group-containing compounds represented by the following formula (I):

wherein $R^1$ represents a hydrogen atom or an alkyl group which may be substituted, and $R^2$ represents an alkyl group which may be substituted or an aryl group which may be substituted;

with alkyl-substituted amines represented by $R^3(R^4)NH$ wherein $R^3$ and $R^4$ each independently represents a hydrogen atom or an alkyl group which may be substituted, provided that both $R^3$ and $R^4$ are not hydrogen atoms at the same time;

in the presence of the dehydrogenase or transformant of the present invention; and a method of producing N-alkyl-amino acid derivatives, which comprises a step of reacting aminocarboxylic acids represented by the following formula (II):

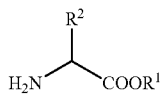

(II)

wherein R¹ represents a hydrogen atom or an alkyl group which may be substituted, and R² represents an alkyl group which may be substituted or an aryl group which may be substituted;

an enzyme capable of converting aminocarboxylic acids represented by the formula (II) to compounds represented by the formula (I):

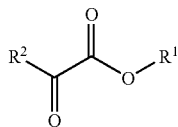

(I)

wherein R¹ and R² are the same as defined in the formula (II); and an alkyl-substituted amine represented by R³(R⁴)NH wherein R³ and R⁴ each independently represent a hydrogen atom or an alkyl group which may be substituted, provided that both R³ and R⁴ are not hydrogen atoms at the same time;

in the presence of the dehydrogenase, polypeptide or transformant of the present invention.

Examples of alkyl groups of R¹ of the formula (I) include straight, branched or cyclic alkyl group which may be substituted with non-reactive group such as a halogen atom and aryl group. Specific examples include methyl, ethyl, n-propyl, isopropyl, trifluoromethyl, and benzyl groups. Those having 1 to 10 carbons among these are preferred, and those having 1 to 4 carbons are more preferred.

R¹ is preferably a hydrogen atom or straight chain alkyl group, most preferably a hydrogen atom.

Examples of alkyl groups of R² include straight, branched or cyclic alkyl group which may be substituted with non-reactive group such as a halogen atom, hydroxyl, or aryl groups. Specific examples include methyl, ethyl, N-propyl, isopropyl, fluoromethyl, trifluoromethyl, hydroxymethyl, and benzyl groups.

Examples of aryl groups of R² include aryl group which may be substituted with non-reactive group such as a halogen atom, hydroxyl, alkyl, or aryl groups. Specific examples include phenyl, toryl, fluorophenyl, and hydroxyphenyl groups.

The alkyl and aryl groups which may be substituted are preferably those having 1 to 10 carbons.

R² is preferably an alkyl, haloalkyl, or aralkyl group. Those having straight chain are particularly preferred.

Preferred specific examples of the compound represented by the formula (I) include pyruvic acid, hydroxypyruvic acid, phenylpyruvic acid, β-fluoropyruvic acid, 2-ketohexanoic acid, 2-ketoisohexanoic acid, 2-oxobutyric acid, 2-ketooctanoic acid, or 2-keto n-valeric acid, and particularly preferably pyruvic acid, phenylpyruvic acid, α-fluoropyruvic acid, 2-oxobutyric acid, 2-ketohexanoic acid, or 2-keto n-valeric acid.

Preferred specific examples of the compound represented by the formula (II) include phenylalanine and methionine.

Amines used in the present invention are those represented by R³(R⁴)NH.

R³ and R⁴ are each independently a hydrogen atom or alkyl group which may be substituted, wherein the alkyl group which may be substituted is straight, branched or cyclic alkyl group which may be substituted with non-reactive group such as a halogen atom, hydroxyl, amino, or aryl groups.

Specific examples of the alkyl groups which may be substituted include methyl, ethyl, n-propyl, isopropyl, fluoromethyl, trifluoromethyl, hydroxymethyl, aminomethyl, and benzyl groups. Straight chain alkyl group or aminoalkyl group is preferred.

The above alkyl groups which may be substituted are preferably those having 1 to 6 carbons, more preferably those having 1 to 4 carbons.

Preferred specific examples of the above amines include methylamine, ethylamine, N-propylamine, isopropylamine, diaminomethane, dimethylamine, and cyclohexanamine, more preferably primary amines, and most preferably methylamine.

In the present reaction, the dicarbonyl group-containing compound which is a reaction substrate, is generally used in the concentration range of 0.01 to 90% w/v, preferably 0.1 to 30% w/v. This may be added all at once at the beginning of reaction, but continuous or intermittent addition is desirable in regards to reducing any substrate inhibition effect of the enzyme and improving accumulation concentration of the product.

In the present reaction, the aminocarboxylic acid which is a reaction substrate, is generally used in the concentration range of 0.01 to 90% w/v, preferably 0.1 to 30% w/v.

Amines are used in equimolar amounts or more, preferably 1.5 times or more molar amounts over dicarbonyl group-containing compounds and aminocarboxylic acids. Provided that it is within the above range and taking pH of the system and cost etc. into consideration, amines can generally be used as necessary. They are generally used in the amount of 50 times molar amounts or less, preferably 20 times molar amounts or less.

In this reaction, when allowing the transformants to act on dicarbonyl group-containing compounds and aminocarboxylic acids, the transformants can be used directly, or transformants treated with organic solvents such as acetone, DMSO and toluene or surfactants; those which are lyophilized; treated cells such as those disrupted physically or enzymatically; fractions from the transformants containing the enzyme of the invention, extracted as a crude or purified product; as well as those immobilized onto carriers represented by, for example polyacrylamide gel and carrageenan gel, can be used.

In the present reaction, it is preferred to add coenzyme NAD+ or NADP+ (hereinafter abbreviated as NAD(P)+) or NADH or NADPH (hereinafter abbreviated as NAD(P)H), generally in the range of 0.001 mM to 100 mM, preferably 0.01 to 10 mM.

When adding the above coenzyme, regeneration of NAD(P)+ produced from NAD(P)H back into NAD(P)H is preferable for improving production efficiency. The regeneration methods include (1) a method utilizing the ability of a host microorganism itself to reduce NAD(P)+; (2) a method of adding microorganisms which have the ability to produce NAD(P)H from a NAD(P)+ or treated cells thereof, or adding enzymes which can be utilized for regeneration of NAD(P)H (regeneration enzyme) such as glucose dehydrogenase, formate dehydrogenase, alcohol dehydrogenase, amino acid dehydrogenase, organic acid dehydrogenase (such as malic acid dehydrogenase) to the reaction system; and (3) a method in which during production of transformants, a gene encoding the above regeneration enzyme that can be utilized for regeneration of NAD(P)H is introduced into a host simultaneously with the DNA of the invention.

In the above method (1), it is preferred to add, for example, glucose, ethanol, or formic acid to the reaction system.

In the above method (2), microorganisms containing the above regeneration enzymes; treated cells thereof, such as the above microorganism cells treated with acetone, lyophilized cells, and physically or enzymatically disrupted cells; enzyme fractions of the present invention extracted as a crude or purified product; as well as cells immobilized onto carriers represented by, for example, polyacrylamide gel and carrageenan gel may be used. Commercially available cells may also be used.

In this case, the amount of the regeneration enzyme used is in particular such an amount that 0.01 to 100 times, preferably approximately 0.5 to 20 times of the enzyme activity can be obtained as compared with the dehydrogenase of the present invention.

It is also required to add compounds which will be a substrate for a regeneration enzyme, for example, glucose when employing glucose dehydrogenase, formic acid when employing formate dehydrogenase, and ethanol or isopropanol when employing alcohol dehydrogenase. The amount added will be 0.1 to 20 times molar amounts, preferably 1 to 5 molar amounts as compared to a dicarbonyl group-containing compounds which is a reaction material.

In the above method (3), a method of incorporating the DNA of the present invention and a DNA of the regeneration enzyme into chromosomes, a method of introducing both DNAs into a single vector and transforming the host therewith, and a method of introducing both DNAs separately into vectors and transforming the host therewith, can be used. When both DNAs are separately introduced into vectors and then the host is transformed, vectors must be selected taking into consideration incompatibility of the vectors to each other.

When multiple genes are introduced into a single vector, it is possible to ligate regions involved in regulation of expression, such as promoters and terminators. It is also possible to express them as operons containing multiple cistrons, such as lactose operon.

The present reaction is conducted in an aqueous medium containing a reaction substrate and the transformant of the invention as well as various coenzymes added, as necessary and its regeneration system, or in a mixture of the above described aqueous medium and organic solvent.

Examples of the aqueous medium include water and buffer solution. Organic solvents in which the reaction substrate is highly soluble, appropriately selected from water-soluble organic solvents such as ethanol, propanol, tetrahydrofuran and dimethyl sulfoxide, and water-insoluble organic solvents such as ethyl acetate, butyl acetate, toluene, chloroform and n-hexane, can be used.

The present invention is generally conducted at reaction temperature of 4 to 50° C., preferably 10 to 40° C. and at pH 6 to 11, preferably pH 7 to 11.

It is also possible to utilize a membrane reactor.

Further, when the compound represented by the formula (I) used as reaction material in the present reaction is a carboxylate ester, a commercially available hydrolase may be allowed to co-exist in the system to convert the substrate into a carboxylic acid where $R^1$ is a hydrogen atom, followed by N-alkylamination.

In the present reaction, the compound represented by the formula (I) may be produced in the system by using aminocarboxylic acids corresponding to the formula (I), i.e. the compound represented by the formula (II) ($R^2CH(NH_2)COOR^1$) as reaction material, and allowing for co-existence of an enzyme capable of acting on the compound represented by the formula (II) and converting it into the compound represented by the formula (I), and may be then N-alkylaminated with the dehydrogenase of the invention.

The enzymes are not particularly limited as long as they are capable of acting on the compound represented by the formula (II) and converting it into the compound represented by the formula (I). Specific examples include amino acid oxidase, amino acid dehydrogenase, and amino acid transferase. Enzymes having broad substrate specificity are preferred. Specific examples include L-amino acid oxidase described in Enzyme and Microbial Technology vol.31 (2002) p 77–87, and D-amino acid oxidase from Sigma Corporation. It is preferred that the amino acid oxidase, amino acid dehydrogenase or amino acid transferase which are used are those which react only on amino acids and which correspond to the coenzyme used in the present reaction, so as to allow for it to be an alternative to the coenzyme regeneration system. In other words, when NAD(P)H is used as a coenzyme for N-alkylamination of the present reaction, NAD(P)H will be converted into NADP+ by N-alkylamination of the present reaction, while when producing the compound represented by the formula (I) from aminocarboxylic acids, this NADP+ is utilized and converted back into NAD(P)H. In addition, when an enzyme capable of acting on the compound represented by the formula (II) and converting it into the compound represented by the formula (I) acts only on amino acids having no substituents on the carboxylate group, an additional enzyme which hydrolyzes the aminocarboxylic acids into amino acids may be allowed to coexist, and the reaction may be carried out after production of the amino acids.

Once the reaction is complete, N-alkyl-amino acid derivatives which is produced from the present reaction may be separated from cells and proteins in the reaction solution by, for example, centrifugation and membrane treatment, followed by suitable combinations of, for example, extraction with organic solvents such as ethyl acetate and toluene, distillation, column chromatography, and crystallization.

(V) Methods of Producing L-cyclic Amino Acid According to the Present Invention

The present invention further relates to a method of producing L-cyclic amino acid, which comprises a step of allowing N-methyl-L-amino acid dehydrogenase or a cell containing the same, a preparation of the cell, or a culture solution obtained by culturing the cell to act on a cyclic amino acid having a double bond at 1-site represented by the following formula (I):

wherein A represent an alkyl chain having a chain length of 1 to 6 atoms, which may includes at least one type of hetero atom selected from the group consisting of a sulfur atom, an oxygen atom and a nitrogen atom in the chain or at the terminal thereof, and may be substituted, so as to generate an L-cyclic amino acid represented by the following formula (II):

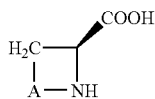

(II)

wherein A represents the same meaning as described above;

a method of producing L-cyclic amino acids which comprises steps of allowing an enzyme capable of converting an amino group at α-site of diamino acid into a keto group to generate α-keto acid to act on a chained α,ω-diamino acid represented by the following formula (III):

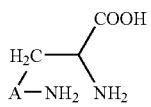

(III)

wherein A represents the same meaning as described above, to generate a cyclic amino acid having a double bond at 1-site represented by the following formula (I):

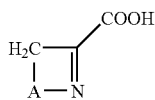

(I)

wherein A represents the same meaning as described above; and generating an L-cyclic amino acid represented by the following formula (II):

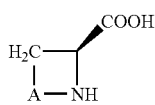

(II)

wherein A represents the same meaning as described above, from the above-obtained cyclic amino acid having a double bond at 1-site by the aforementioned method; and a method of producing L-cyclic amino acids which comprises steps of allowing an enzyme capable of oxidizing an amino group at 1-site to act on a cyclic amino acid represented by the following formula (IV):

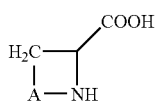

(IV)

wherein A represents the same meaning as described above, to generate a cyclic amino acid having a double bond at 1-site represented by the following formula (I):

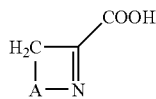

(I)

wherein A represents the same meaning as described above; and generating an L-cyclic amino acid represented by the following formula (II):

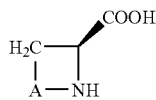

(II)

wherein A represents the same meaning as described above, from the above-obtained cyclic amino acid having a double bond at 1-site by the aforementioned method.

In the aforementioned formulae (I), (II), (III) and (IV), the specific explanation will be given about the atom and group in the definition of A.

In the present invention, examples of the alkyl chain include liner or branched alkyl chains having 1 to 6 carbons such as —$CH_2$—, —$C_2H_4$—, —$C_3H_6$—, —$C_2H_3CH_3$—, —$C_4H_8$—, —$C_3H_5CH_3$—, —$CH_2CHCH_3CH_2$—, —$C_5H_{10}$—, —$C_4H_7CH_3$—, —$C_2H_4CHCH_3CH_2$—, —$CH_2CHCH_3C_2H_4$—, —$CH_2C(CH_3)_2CH_2$— and —$C_6H_{12}$—. Among them, linear alkyl chains having 2 to 4 carbons that can form a 5- to 7-membered cyclic amino acid are preferable. In particular, such cases that number of carbons is 2 where a 5-membered amino acid such as L-Proline is formed, number of carbons is 3 where a 6-membered amino acid such as L-pipecolic acid is formed, and that number of carbons is 4 where a 7-membered amino acid such as azepane-2-carboxylic acid is formed, are particularly preferable. The chemical formulae of these compounds are represented below.

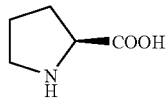 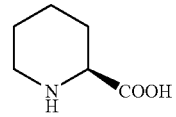

L-Proline  L-pipecolic acid

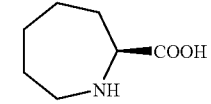

azepane-2-carboxylic acid

The aforementioned alkyl chains may contain a hetero atom such as a sulfur atom, an oxygen atom or a nitrogen atom in the chain or at a terminal thereof. The alkyl chain containing such a hetero atom can form a heterocycle. Plural types or Plural numbers of hetero atoms such as a sulfur atom, an oxygen atom or a nitrogen atom may bes contained in the alkyl chain. Preferable number of the contained hetero atom is from 1 to 3. Examples of the alkyl chain containing a hetero atom include —CHOHCH$_2$—, —CH$_2$CHOHCH$_2$—, —SCH$_2$—, —SC$_2$H$_4$—, —SC$_3$H$_6$—, —OCH$_2$—, —OC$_2$H$_4$—, —OC$_3$H$_6$—, —NHCH$_2$—, —NHC$_2$H$_4$—, —NHC$_3$H$_6$—, —NHCH$_2$CHCOOH—, —C$_2$H$_4$NHCO—, —C$_2$H$_4$NHCN—, —C$_2$H$_4$CHCOOH—, —SCH$_2$CHCOOH—, —SC$_2$H$_4$CHCOOH—, —C$_3$H$_6$NHCH$_2$CHCOOH—, —NHCHCOOHCH$_2$— and —CH$_2$NHCHCOOHC$_2$H$_4$.

In the case where A is an alkyl chain containing a sulfur atom, examples of the optically active cyclic amino acid include thioproline, 3-thiomorpholine carboxylic acid and [1,4]thiazepane-3-carboxylic acid. In the case where A is an alkyl chain containing an oxygen atom, examples of the optically active amino acid include 4-oxazolidine-carboxylic acid and 3-morpholine carboxylic acid. In the case where A is an alkyl chain containing plural nitrogen atoms, example of the optically active cyclic amino acid includes piperazine-2-carboxylic acid. The chemical formulae of these compounds are represented below.

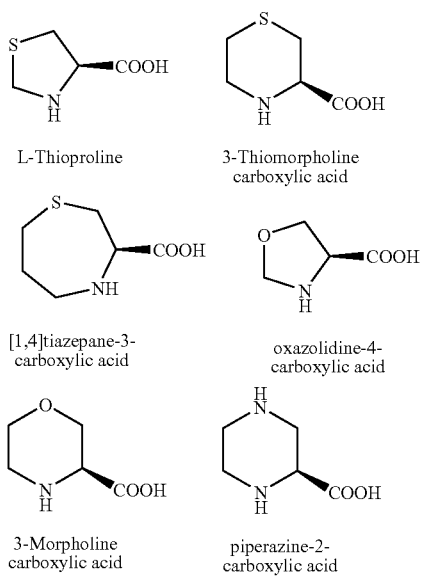

A substituent on the aforementioned alkyl chain or alkyl chain containing hetero atom is not limited particularly, so long as it does not give an adverse effect to the reaction, and examples thereof include an alkyl group, an aryl group, an alkoxy group, a carboxyl group, a halogen group, a cyano group, an amino group, a nitro group and a hydroxyl group. Examples of the cyclic amino acid containing a substituent include hydroxyproline and hydroxypipecolic acid. Chemical formulae of them are represented below.

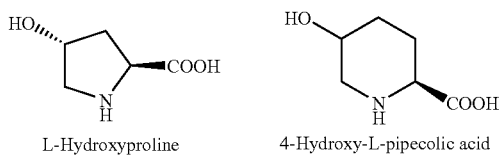

N-methyl-L-amino acid dehydrogenase in the present invention means an enzyme, as is typified by N-methyl-L-amino acid dehydrogenase derived from *Pseudomonas putida* ATCC12633 strain, that generates N-methyl-L-amino acid such as N-methyl-L-alanine and N-methyl-L-phenylalanine by adding methyl amine to α-keto acid such as pyruvic acid and phenylpyruvic acid while employing reduced nicotinamide adenine dinucleotide (NADH) or reduced nicotinamide adenine dinucleotide phosphate (NADPH) (hereinafter, sometimes abbreviated as "NAD(P) H" lumping both of them) as a coenzyme (refer to the following reaction formula).

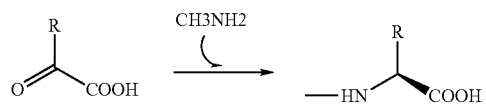

As for the cyclic amino acid having a double bond at 1-site represented by the following formula (I), which is to be reduced by using N-methyl-L-amino acid dehydrogenase and is a substrate in a cyclic amino acid-generating reaction, (I)

wherein A is of the same meaning as described above, one that is produced by any means may be used.

For example, it can be biologically or chemically derived from corresponding diamino acid or racemic cyclic amino acids.

In the case where it is derived from diamino acid, as shown by the following reaction formula, when an amino group at α-site of diamino acid is converted into a keto group to produce α-keto acid, the α-keto acid is subjected to non-enzymatic dehydration ring closure to become a cyclic amino acid having a double bond at 1-site. Here, in the following reaction formula, A is of the same meaning as described above.

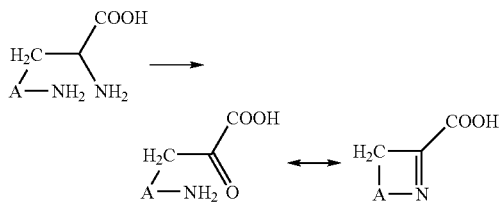

Usually, since the α-keto acid and the cyclic amino acid having a double bond at 1-site exist as a mixture in equilibrium in an aqueous solution, they are presumed as equivalent ones. That is, in the reaction system of the present invention, the cyclic amino acid having a double bond at 1-site itself, or a mixture of the α-keto acid and the cyclic amino acid having a double bond at 1-site, or the α-keto acid may be added or incorporated. Any of these embodiments is included in the present invention.

As for a catalyst that catalyzes the above reaction, any catalyst may be usable without particular limitations, so long as it can convert an amino group at α-site of diamino acid into a keto group to generate α-keto acid. Specific examples thereof include enzymes such as amino acid oxidases (D-amino acid oxidase, L-amino acid oxidase), amino acid dehydrogenases (D-amino acid dehydrogenase, L-amino acid dehydrogenase) and amino acid transferases (D-amino acid aminotransferase, L-amino acid aminotransferase).

Among these, enzymes that have a wide substrate specificity are preferable. Specific examples thereof include L-amino acid oxydase described in Enzyme and Microbial Technology vol. 31 (2002) p 77–87, D-amino acid oxydase manufactured by Sigma and the like.

As amino acid oxydase, amino acid dehydrogenase and amino acid transferase to be used, those which react only on diamino acid and and correspond to a coenzyme for use in the present reaction are preferred, since it can serve as a substitution for the regeneration system of the coenzyme. That is, in the reduction reaction of the present reaction, in the case where NAD(P)H is used as a coenzyme, the NAD(P)H becomes oxydized nicotinamide adenine nucleotide (NAD$^+$) or oxydized nicotinamide adenine dinucleotide phosphate (NADP$^+$) (sometimes abbreviated as "NAD(P)$^+$" lumping both of them) along with reduction in the present reaction but, on the other hand, the NAD(P)$^+$ is utilized to be converted into NAD(P)H upon producing cyclic amino acid having a double bond at 1-site from diamino acids.

Further, when producing cyclic amino acids having a double bond at 1-site from racemic cyclic amino acid compounds, it is possible to use either a reaction in which a cyclic amino acid having optical activity different from that of the finally generating optically active cyclic amino acid is oxidized selectively to generate a cyclic amino acid having a double bond at 1-site, or a reaction in which both of them are lead to a cyclic amino acid having a double bond at 1-site.

That is, as described in the reaction formula below, a method may be used in which a cyclic amino acid with the desired optical activity, that is L-cyclic amino acid, is remained as it is, and that with the opposite optical activity from wish, that is D body, is converted into a cyclic amino acid having a double bond at 1-site, which is then reduced by using N-methyl-L-amino acid dehydrogenase of the invention; or both of them may be converted into cyclic amino acids having a double bond at 1-site, followed by isolation to be used for the subsequent reduction reaction. Here, in the following reaction formulae, A is of the same meaning as described above.

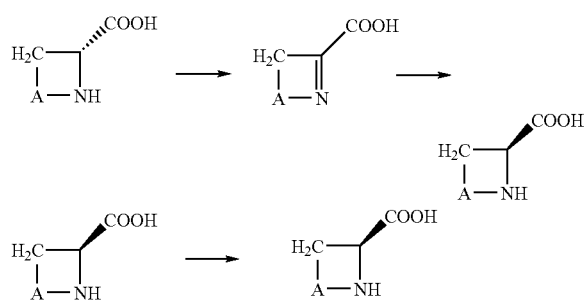

As for a catalyst that converts an optically active body of D body into a cyclic amino acid having a double bond at 1-site, any one having the activity may be used without particular limitations, and an enzyme is used preferably. Examples of the enzyme include D-amino acid oxidase, D-amino acid dehydrogenase, D-amino acid aminotransferase and the like.

Among them, an enzyme having a wide substrate specificity is preferable. Specifically, the D-amino acid oxydase manufactured by Sigma and the like can be mentioned.

As amino acid oxydase, amino acid dehydrogenase and amino acid transferase to be used, those that react only in the case where an optically active body of D body is converted into a cyclic amino acid having a double bond at 1-site, and correspond to a coenzyme for use in the present reaction, are preferred, since it can serve as a substitution for the regeneration system of the coenzyme. That is, in the reduction reaction of the present reaction, in the case where NAD(P)H is used as a coenzyme, the NAD(P)H becomes NAD(P)$^+$ along with reduction in the present reaction but, on the other hand, the NAD(P)$^+$ is utilized to be converted into NAD(P)H upon producing a cyclic amino acid having a double bond at 1-site from an optically active body of the opposite optical activity from wish.

When various kinds of amino acid oxydases are used for obtaining a cyclic amino acid having a double bond at 1-site, since hydrogen peroxide may be generated along with the reaction to give such an adverse effect as decrease in enzyme activity on the reaction, a combination of another enzyme is also desirable in order to remove the hydrogen peroxide from the reaction system. As for an enzyme for removing the hydrogen peroxide, any enzyme may be usable without particular limitations, so long as it reacts on hydrogen peroxide. Specifically, catalase and peroxidase are preferable. There is no limitation on the amount to be added as long as the generating hydrogen peroxide is removed effectively and, specifically, the enzyme is used in a range of from 0.1 to 1,000,000 times activity, preferably from 1 to 100,000 times activity relative to the oxidase.

In addition, when oxidase is used, the activity can be enhanced by addition of flavin adenine dinucleotide (FAD), which is a coenzyme. Addition concentration thereof is in a range of from 0.00001 to 100 mmol, preferably from 0.001 to 10 mmol in the reaction solution.

In the production method of the invention, concentration of the cyclic amino acid having a double bond at 1-site, which acts as a reaction substrate, in the reaction solution is usually in a range of 0.0001 to 90% w/v, preferably 0.01 to 30% w/v. They may be added in a lot at the start of the reaction, but, from the viewpoint of reducing effect of substrate inhibition of the enzyme, if any, and enhancing accumulation concentration of the products, continuous or intermittent addition is desirable.

When diamino acids are used as the reaction substrate, usually, substrate concentration is in a range of 001 to 90% w/v, preferably 0.1 to 30% w/v.

When racemic cyclic amino acids are used as the substrate, usually, substrate concentration is in a range of 0.01 to 90% w/v, preferably 0.1 to 30% w/v.

Further, in the present reaction, a coenzyme NAD(P)$^+$ or NAD(P)H is preferably added usually by 0.001 mM to 100 mM, and preferably by from 0.01 to 10 mM.

The present invention will now be described in more detail with reference to Examples, but the present invention is not to be limited thereto.

EXAMPLES

Enzyme activity in the Examples of the present invention was measured in the following manner.

To a crude enzyme solution to be measured, sodium phenylpyruvate (final concentration 15 mM), methylamine-sulfate buffer (pH 10, final concentration 400 mM), and NADPH (final concentration 10 mM) were added to a total volume of 50 µL. The mixture was allowed to react at 37° C. for 1 hour. After the reaction was completed, 5 µL of 10% trichloroacetic acid was added and the mixture was centrifuged at 13000 rpm for 5 minutes. 10 µL of the supernatant was diluted in 40 µL of high performance liquid chromatography (hereinafter abbreviated as HPLC) eluant, filtered through a 0.45 µm filter, and then analyzed by high performance liquid chromatography (hereinafter abbreviated as HPLC).

HPLC conditions were:

Column: Ultron ESPh-CD (Shinwa Chemical Industries, LTD.)

Temperature: 40° C.

Eluant: 20% acetonitrile, 80% 20 mM $KH_2PO_4$, $H_3PO_4$, 0.4 mL/L (pH 3)

Flow rate: 0.85 mL/min.

Detector: UV detector (210 nm)

Reagents from Sigma Corporation were used as standard samples.

Activity unit of enzyme, 1 unit is defined as the amount of an enzyme capable of producing 1 µmol of N-methylphenylalanine per minute.

Example 1

Purification of Enzyme (1-1)

*Pseudomonas putida* ATCC 12633 strain was inoculated into 2×100 mL sterilized liquid medium (containing 5 g/L of methylamine hydrochloride, 1 g/L of glucose, 5 g/L of yeast extract, 7 g/L of dipotassium hydrogenphosphate, 3 g/L of potassium dihydrogenphosphate, and 0.1 g/L of magnesium sulfate heptahydrate) (in 500-mL Sakaguchi flasks), and aerobically cultivated with shaking at 28° C. for 18 hours (first preculture). Next, 50 mL of the culture obtained from the first preculture was inoculated into each of 4×2-L Sakaguchi flasks containing 500 mL of sterilized liquid medium of the same composition (in 2 L Sakaguchi flasks), and cultured with shaking under aerobic condition at 28° C. for 8 hours (second preculture). 200 liters of a medium supplemented with 1% polypeptone (Nacalai Tesque, Inc.), 0.5% yeast extract (Nacalai Tesque, Inc.), and 1% sodium chloride (Nacalai Tesque, Inc.) (hereinafter abbreviated as LB medium) was sterilized, inoculated with all 2200 mL of the culture obtained in the second preculture, and aerobically cultured at 28° C. for 16 hours (main culture). The culture obtained after cultivation was centrifuged to obtain 2.5 kg of wet cells. The cells were suspended in 5 L of 20 mM Tris-hydrochloride buffer (pH 7.0) and ultrasonicated to obtain 5.9 L of crude enzyme solution.

Ammonium sulfate fractionation was performed on the crude enzyme. Activity was found in the fractions containing 20 to 60% concentration of ammonium sulfate. These fractions were collected and dialyzed 5 times against 15 L of 20 mM Tris-hydrochloride buffer (pH 7.0). The amount of the enzyme solution was 3100 mL.

(1-2) Purification by SuperQ-TOYOPEARL (TOSOH Corporation)

3100 mL of the fractions from 20 to 60% saturated ammonium sulfate fractionation was subjected to 700 mL of SuperQ-TOYOPEARL (TOSOH Corporation) equilibrated with 20 mM Tris-hydrochloride buffer (pH 7.0). This was then washed with 4900 mL of 20 mM Tris-hydrochloride buffer (pH 7.0). No activity was detected in the wash fraction.

Following washing, elution with 3500 mL of 20 mM Tris-hydrochloride buffer containing 0.2 M sodium chloride was performed. Protein having activity was eluted under this condition. Elution with 3500 mL of 20 mM Tris-hydrochloride buffer containing 0.5 M sodium chloride was further performed, but no activity was detected in this fraction.

The fractions eluted with 20 mM Tris-hydrochloride buffer containing 0.2 M sodium chloride were recovered, and the amount of protein and the enzyme activity were measured. 3900 mL of the solution showing activity was dialyzed 3 times against 12 L of 20 mM Tris-hydrochloride buffer containing 20% saturated ammonium sulfate (pH 7.0). The amount of the enzyme solution after dialysis was 3000 mL.

(1-3) Purification by Butyl-TOYOPEARL (TOSOH Corporation)

3000 mL of the enzyme solution obtained in (1-2) was subjected to 500 mL of Butyl-TOYOPEARL (TOSOH Corporation) equilibrated with 20 mM Tris-hydrochloride buffer containing 20% saturated ammonium sulfate (pH 7.0). This was then washed with 2800 mL of 20 mM Tris-hydrochloride buffer (pH 7.0) containing 20% saturated ammonium sulfate. Upon measurement of the wash fraction for the amount of protein and the enzyme activity, activity was detected in this fraction. Ammonium sulfate was added directly to the enzyme solution obtained by washing to obtain fractions having a concentration of 5 to 20% saturated ammonium sulfate, and the fractions were subjected again to Butyl-TOYOPEARL.

(1-4) Second Purification by Butyl-TOYOPEARL (TOSOH Corporation)

5700 mL of the enzyme solution obtained from the ammonium sulfate fractions was subjected to 500 mL of Butyl-TOYOPEARL (TOSOH Corporation) equilibrated with 20 mM Tris-hydrochloride buffer (pH 7.0) containing 30% saturated ammonium sulfate. It was then washed with 2300 mL of 20 mM Tris-hydrochloride buffer (pH 7.0) containing 30% saturated ammonium sulfate. Upon measurement of the wash fraction for the amount of protein and the enzyme activity, activity was detected in this fraction. The column was then eluted with 20 mM Tris-hydrochloride buffer (pH 7.0) containing 15% saturated ammonium sulfate. Activity was detected in the eluate as well. Both of the above fractions showing activity was collected, 3070 g of ammonium sulfate was added to achieve 60% saturated concentration and stirred, and then concentrated. The amount of the resulting enzyme solution was 600 mL. This was dialyzed 3 times against 14 L of 20 mM Tris-hydrochloride buffer (pH 7.0), and the amount of the enzyme solution obtained was 1000 mL.

(1-5) Purification by DEAE-TOYOPEARL (TOSOH Corporation)

1000 mL of the enzyme solution obtained by dialysis in (1-4) was subjected to 600 mL of DEAE-TOYOPEARL (TOSOH Corporation) equilibrated with 20 mM Tris-hydrochloride buffer (pH 7.0). It was then washed with 4000 mL of 20 mM Tris-hydrochloride buffer (pH 7.0). No activity was seen in the wash fraction. It was then eluted with 2500 mL of 20 mM Tris-hydrochloride buffer (pH 7.0) containing 0.1 M sodium chloride. Almost no activity was detected in the resulting fraction. Subsequently, the protein was eluted using a sodium chloride gradient at concentrations from 0.1 to 0.3 M. Upon collection of fractions having enzyme activity, 1700 mL of enzyme solution was obtained. To this enzyme solution, 760 g of ammonium sulfate was added, and the mixture was stirred and then concentrated. The resulting enzyme solution was in a volume of 60 mL. This was dialyzed 2 times against 8 L of 20 mM Tris-hydrochloride buffer (pH 7.0). The amount of the enzyme solution after dialysis was 100 mL.

(1-6) Purification by Green-sepharose CL-4B 150 mL of commercially available swollen Sepharose CL-4B gel was taken up onto a glass filter and washed by siphonage using 1 L of distilled water. This was transferred into a 2-L Sakaguchi flask. To this, 0.75 g of Reactive Green 19 (Sigma Corporation) dissolved in 150 mL of water was added (ratio is 7.5 mg of dye/1 mL of gel). Next, 15 mL of 22% aqueous sodium chloride was added (final concentration: approximately 2%), and then stirred with enough shaking for the gel and the dye to be mixed well for approximately 30 minutes. 1.5 g of crystalline sodium carbonate was added and stirred with shaking at 50° C. overnight. Once the reaction was complete, gel suspension was transferred onto a glass filter, and the dye-gel was washed with water (approximately 1.5 L), 1 M aqueous sodium chloride (approximately 1.5 L), and water (approximately 3 L) in this order until no color was seen in the filtrate, to prepare Green-sepharose CL-4B.

450 mL of Green sepharose CL-4B prepared according to the method above was equilibrated with 20 mM Tris-hydrochloride buffer (pH 7.0), and 100 mL of the enzyme solution obtained in (1-5) was run.

This was then washed with 3000 mL of 20 mM Tris-hydrochloride buffer (pH 7.0). Approximately 15% of the total activity measured with the enzyme solution obtained in (1-5) was detected in the wash fraction. Subsequently, the protein was eluted using a sodium chloride gradient at concentrations from 0 to 3 M. Upon collection of fractions having enzyme activity, 231 mL of the enzyme solution was obtained. To this, 109 g of ammonium sulfate was added to achieve a concentration of 70% saturation, and the protein was precipitated. The precipitate was suspended in 3 mL of 20 mM Tris-hydrochloride buffer (pH 7.0), and dialyzed against 9 L of 20 mM Tris-hydrochloride buffer (pH 7.0) containing 20% saturated ammonium sulfate for 8 hours. After dialysis, precipitate found left in the tube was suspended in 8.5 mL of buffer used for dialysis. Since the precipitate was not dissolved even after this process, centrifugation was performed to separate the precipitate and the supernatant. Because most of the activity was seen in the supernatant, 13 mL the supernatant was purified with RESOURCE PHE (Amersham Biosciences). The protein was eluted by a gradient using 20 mL of 20 mM Tris-hydrochloride buffer (pH 7.0) containing 20% saturated ammonium sulfate and 20 mL of 20 mM Tris-hydrochloride buffer (pH 7.0).

19 mL of the collected enzyme solution was concentrated to 5 mL by ultrafiltration, and then dialyzed against 20 mM Tris-hydrochloride buffer (pH 7.0) to obtain 6.5 mL of enzyme solution.

(1-7) Purification by Blue-Sepharose 4B (Amersham Biosciences)

5 mL of Blue-sepharose 4B (Amersham Biosciences) was equilibrated with 20 mM Tris-hydrochloride buffer (pH 7.0), and 6.5 mL of the enzyme solution obtained in (1-6) was run. This was then washed with 50 mL of 20 mM Tris-hydrochloride buffer (pH 7.0). The active fractions were further eluted with a sodium chloride gradient at concentrations from 0 to 1 M using 50 mL of 1 M aqueous sodium chloride and 50 mL of 20 mM Tris-hydrochloride buffer (pH 7.0).

Specific activity and the like of the enzyme fractions obtained in each purification step of the above (1-1) to (1-7) are summarized in Table 1.

TABLE 1

| Purification step | Total activity (U) | Specific activity (U/mg) | Total protein (mg) | Recovery of activity (%) | Degree of Purification (times) |
|---|---|---|---|---|---|
| Crude enzyme | 4700 | 0.045 | 110,000 | 100 | 1 |
| Ammonium sulfate fraction | 4500 | 0.051 | 87,000 | 96 | 1.1 |
| SuperQ-TOYO PEARL | 760 | 0.043 | 18,000 | 16 | 0.96 |
| Butyl-TOYOPEARL | 750 | 0.042 | 18,000 | 16 | 0.93 |
| Butyl-TOYOPEARL | 400 | 0.03 | 13,000 | 8 | 0.67 |
| DEAE-TOYO PEARL | 280 | 0.094 | 2,900 | 6 | 2.1 |
| Green-sepharose CL-4B | 69 | 2.8 | 25 | 1.5 | 62 |
| RESOURCE PHE | 5.7 | 3.1 | 1.9 | 0.12 | 69 |
| Blue-sepharose 4B | 3.1 | 6.8 | 0.46 | 0.066 | 150 |

Example 2

SDS-PAGE and Analysis of Partial Amino Acid Sequence

All the samples from the respective enzyme purification steps were subjected to SDS-polyacrylamide gel electrophoresis.

A band at approximately 35 to 40 kDa, which increased in amount with the degree of purification, was excised by ordinary methods, and amino acid sequence analysis by Edman method was performed on a protein sequencer to determine the N-terminal amino acid sequence. The sequence is shown as SEQ ID No. 3 in the sequence listing.

The results of BLAST SEARCH suggested that this protein was highly homologous to malate dehydrogenase.

Example 3

Cloning of Enzyme Gene

Chromosomal DNA was prepared from *Pseudomonas putida* ATCC 12633 strain by cultivating it in LB medium and treating the obtained cells with DNeasy Tissue Kit (Qiagen).

Primers were synthesized based on the nucleotide sequence encoding the N-terminal amino acid sequence determined in Example 2 and the amino acid sequence found from BLAST SEARCH. The respective nucleotide sequences are shown as SEQ ID No. 4 (NMPDHf) and 5 (NMPDHr1) in the sequence listing.

Using the chromosomal DNA from *Pseudomonas putida* ATCC 12633 strain as a template, 30 cycles of PCR (98° C., 20 seconds; 68° C., 3 minutes) were carried out using NMPDHf and NMPDHr1 as primers to obtain specifically amplified samples.

The DNA fragments obtained above were introduced into a cloning vector pET21a (Takara Shuzo Co. Ltd.) according to ordinary methods (this plasmid was designated as pENMadh).

Then, *Escherichia coli* (*Escherichia coli*) BL21 (DE3) (Novagen) was transformed.

The transformants were grown on LB medium plates (LB medium+2% agar) containing ampicillin (100 μg/mL) at 37° C. A few of the white colonies which emerged were cultivated, and plasmids were extracted under ordinary conditions. The plasmids obtained were cleaved with restriction enzymes NdeI and HindIII (37° C., 3 hours), and insertion of the object DNA fragments into plasmids was confirmed by agarose electrophoresis.

Colonies thought to have object DNA fragments inserted were cultivated in liquid LB medium containing ampicillin. After 14 hours of cultivation, IPTG was added to make 0.1 mM. Cells were cultivated for additional 3 hours and then collected. The cells were ultrasonicated to obtain a crude enzyme.

Activity of the crude enzyme obtained was measured, and expression of the object protein was confirmed.

Production of N-methyl-phenylalanine was confirmed using the crude enzyme obtained from the colonies carrying the object fragments, whereas no production of N-methyl-phenylalanine was observed in disrupted cells transformed only with the plasmids.

The nucleotide sequence of the fragments inserted in the plasmids, for which activity was confirmed, was analyzed. The nucleotide sequence of the gene and the amino acid sequence of the protein encoded by the gene are shown as SEQ ID No. 2 and SEQ ID No. 1 in the sequence listing, respectively.

Example 4

Synthesis of N-methyl-phenylalanine Using the Cell-free Extract of Transformants 5 mL of LB medium was placed in a test tube, and was steam sterilized at 121° C. for 20 minutes. The medium was cooled to room temperature, to which 5 μL of 100 mg/ml ampicillin in water was then added. A colony of cloned *Escherichia coli* cells obtained in Example 3 was aseptically inoculated into the medium with a platinum loop, and cultivated with shaking at 37° C. for 24 hours (second preculture). Next, 50 mL of LB medium was placed into a 500-mL Sakaguchi flask and sterilized. The medium was cooled to room temperature, to which 50 μL of 100 mg/ml ampicillin in water was then added. 0.5 mL of cloned *Escherichia coli* cell cultures obtained from the second preculture was inoculated into the medium and cultivated with shaking at 37° C. for 10 hours. 50 μL of 1 M IPTG in water was added at this point in time, and cultivation was conducted at 37° C. for further 3 hours. After cultivation, cells were collected by centrifugation and washed twice in 20 mM Tris-hydrochloride buffer (pH 7.0). 0.37 g of the cells obtained was suspended in 8.0 mL of 20 mM Tris-hydrochloride buffer (pH 7.0), and the cells were disrupted by ultrasonication. Cellular debris was removed by centrifugation to obtain 8.0 mL of a cell-free extract.

In a 50-mL beaker, 5.88 ml of 40 mM Tris-hydrochloride buffer (pH 8.0) containing 60 mg of sodium phenylpyruvate, 2.3 mg of NADPH, 35 U of glucose dehydrogenase, and 1 g of glucose was placed, to which 5.88 mL of 240 mM methylamine adjusted to pH 8.0 with sulfuric acid and 3.25 mL of the above cell-free extract were added, and the mixture was allowed to react at 30° C. The reaction was conducted while stirring and adjusting pH to 8.0 with 1 N aqueous sodium hydroxide solution. A portion of the reaction solution was analyzed by HPLC at regular intervals. When the substrate sodium phenylpyruvate was depleted, an additional 30 mg was added and the reaction was continued. This process was repeated 8 times during the reaction of 24 hours. Upon completion of the reaction, the amount of N-methylphenylalanine produced was 146 mg.

Example 5

Purification of Enzyme from Transformants 5 mL of LB medium was placed in a test tube and was steam sterilized at 121° C. for 20 minutes. The medium was cooled to room temperature, to which 5 μL of 100 mg/ml ampicillin in water was then added. A colony of cloned *Escherichia coli* cells obtained in Example 3 was aseptically inoculated into the medium with a platinum loop, and cultivated with shaking at 37° C. for 24 hours (second preculture). Next, 500 mL of LB medium was placed into a 2-L Sakaguchi flask and sterilized. The medium was cooled to room temperature, to which 500 μL of 100 mg/ml ampicillin in water was then added. 0.5 mL of cloned *Escherichia coli* cell cultures obtained from the second preculture was inoculated into the medium and cultivated with shaking at 37° C. for 14 hours. 500 μL of 1 M IPTG in water was added at this point in time, and cultivation was continued at 37° C. for further 3 hours. After cultivation, cells were collected by centrifugation and washed twice with 20 mM Tris-hydrochloride buffer (pH 7.0). 3.3 g of the cells obtained were suspended in 28 mL of 20 mM Tris-hydrochloride buffer (pH 7.0) (total volume 30 ml), and the cells were disrupted by ultrasonication. Cellular debris was removed by centrifugation to obtain 29 mL of a cell-free extract. Subsequently, purification was conducted with Green sepharose CL-4B used in Example 1.

Green sepharose CL-4B (resin amount 100 ml) was equilibrated with Tris-hydrochloride buffer (pH 7.0), and then the above cell-free extract was run.

This was then washed with 800 mL of 20 mM Tris-hydrochloride buffer (pH 7.0). Subsequently, the protein was eluted from the wash fraction using a sodium chloride gradient at concentrations from 0 to 1 M. The fractions having enzyme activity were collected and concentrated using Centriprep (Amersham Biosciences). This was dialyzed against 20 mM Tris-hydrochloride buffer (pH 7.0) for 8 hours. The amount of the enzyme solution after dialysis was 59 ml.

Next, purification by DEAE-TOYOPEARL (TOSOH Corporation) was conducted.

The enzyme solution obtained from the above dialysis was subjected to DEAE-TOYOPEARL (TOSOH Corporation) (60 mL of resin) equilibrated with 20 mM Tris-hydrochloride buffer (pH 7.0). This was then washed with 500 mL of 20 mM Tris-hydrochloride buffer (pH 7.0). Subsequently, the protein was eluted using a sodium chloride gradient at concentrations from 0 to 0.35 M. The fractions having enzyme activity were collected and concentrated using Centriprep (Amersham Biosciences), and then dialyzed against 20 mM Tris-hydrochloride buffer (pH 7.0). The amount of the enzyme solution after dialysis was 6 mL.

The ratios of specific activity of the enzyme fractions from the respective purification steps above are summarized in Table 2.

TABLE 2

| Purification step | Total activity (U) | Specific activity (U/mg) | Total protein (mg) | Recovery of activity (%) | Degree of purification (times) |
|---|---|---|---|---|---|
| Crude enzyme (cell-free extract) | 1900 | 6.3 | 300 | 100 | 1 |
| Green-Sepharose | 840 | 20 | 41 | 44 | 3.2 |
| DEAE-TOYOPEARL | 430 | 27 | 16 | 23 | 4.3 |

Example 6

Substrate Specificity of the Present Enzyme

Purified form of the present enzyme was obtained from cloned *Escherichia coli* cells in the same way as in Example 5.

Enzyme activity was measured by adding thereto various keto acids shown in Table 3 to a final concentration of 10 mM, NADPH to a final concentration of 0.2 mM, and methylamine adjusted to pH 10 with sulfuric acid to a final concentration of 60 mM, and examining the change in absorbance of the reaction mixture at 340 nm. The reaction temperature during measurement was 37° C. Defining the activity of the enzyme when β-phenylpyruvic acid was used as the substrate as 100%, the results are shown in Table 3 for relative activity.

TABLE 3

| Substrate | Relative activity |
|---|---|
| phenylpyruvic acid | 100% |
| pyruvic acid | 334% |
| 2-ketohexanoic acid | 174% |
| 2-ketobutyric acid | 98% |
| β-fluoropyruvic acid | 90% |
| 2-keto-n-valeric acid | 53% |
| Ketoleucine | 30% |
| 2-ketooctanoic acid | 25% |

Example 7

Measurement of Optimal pH

Purified form of the present enzyme was obtained from cloned *Escherichia coli* cells in the same way as in Example 5.

Enzyme activity was measured by adding thereto β-phenylpyruvic acid to a final concentration of 10 mM, NADPH to a final concentration of 0.2 mM, and methylamine adjusted to various pH values with sulfuric acid to a final concentration of 60 mM, and examining the change in absorbance of the reaction solution at 340 nm. The reaction temperature during measurement was 37° C. Defining the amount of enzyme that react with 1 micromole of β-phenylpyruvic acid per minute as 1 unit, the results are shown in FIG. 1 for the relationship between the number of units per protein amount (u/mg) and pH. The optimal pH of the reaction was 10.0.

Example 8

Optimal Working Temperature for the Enzyme

Figure 2:
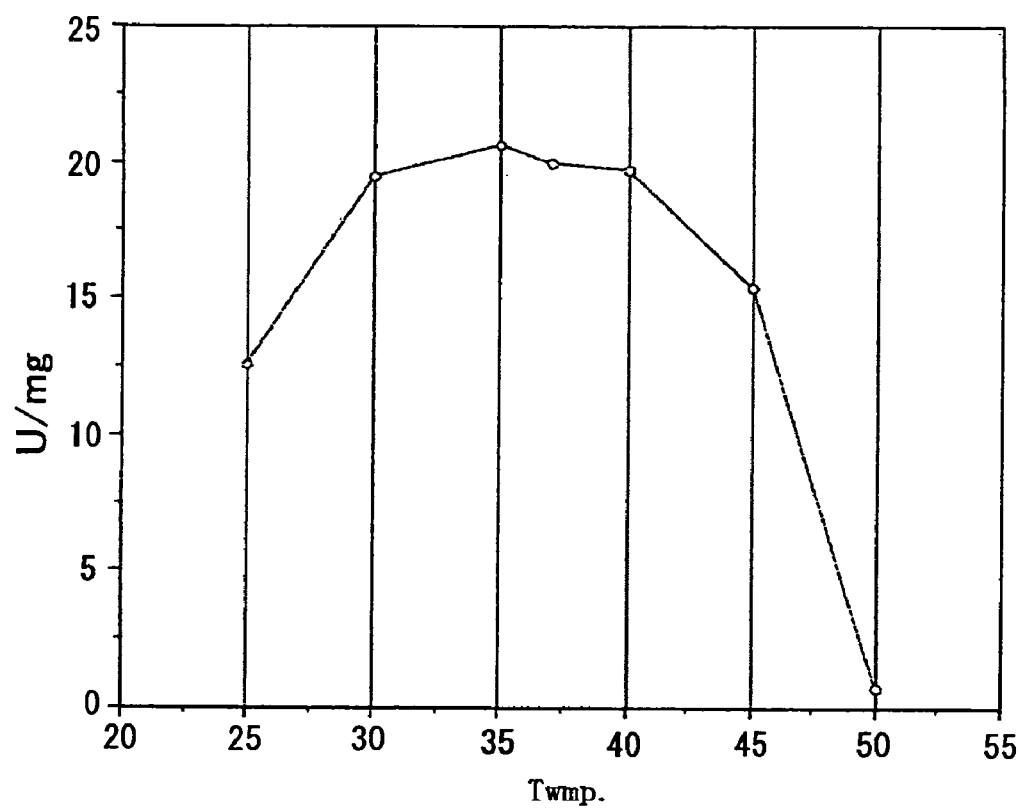
FIG. 2 is a graph showing the optimal temperature for the N-methyl-L-phenylalanine dehydrogenase of the present invention.

Activity was measured using the same reaction conditions as in Example 6 and with methylamine-sulfuric acid (pH 10), except that the temperature was varied. The results are shown in FIG. 2. The optimal temperature was 30 to 40° C.

Example 9 pH Stability

Figure 3:
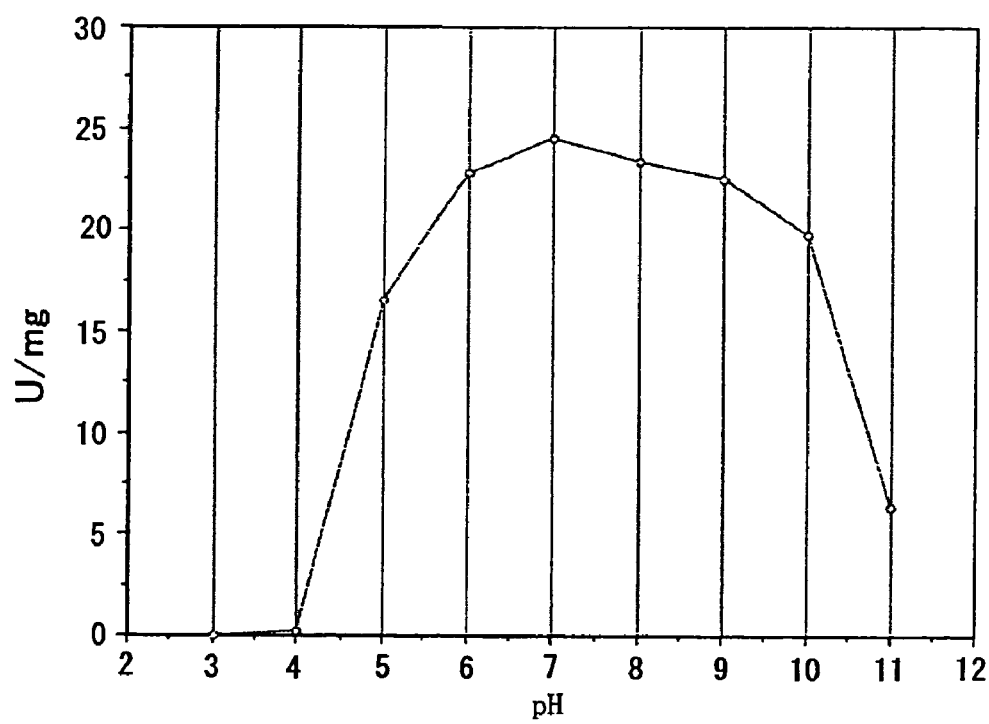
FIG. 3 is a graph showing pH stability of the N-methyl-L-phenylalanine dehydrogenase of the present invention.

Purified enzyme obtained in Example 5 was incubated at various pH values using buffers at 30° C. for 30 minutes, and then the remaining activity was measured. Reaction condition was the same as in Example 7, in which methylamine-sulfuric acid (pH 10) was used and the reaction was conducted at 37° C. The results are shown in FIG. 3 as remaining activity, with the activity of untreated enzyme defined as 100. The enzyme according to the present invention was most stable at pH 6 to 9.

Example 10

Thermal Stability of the Enzyme

Figure 4:
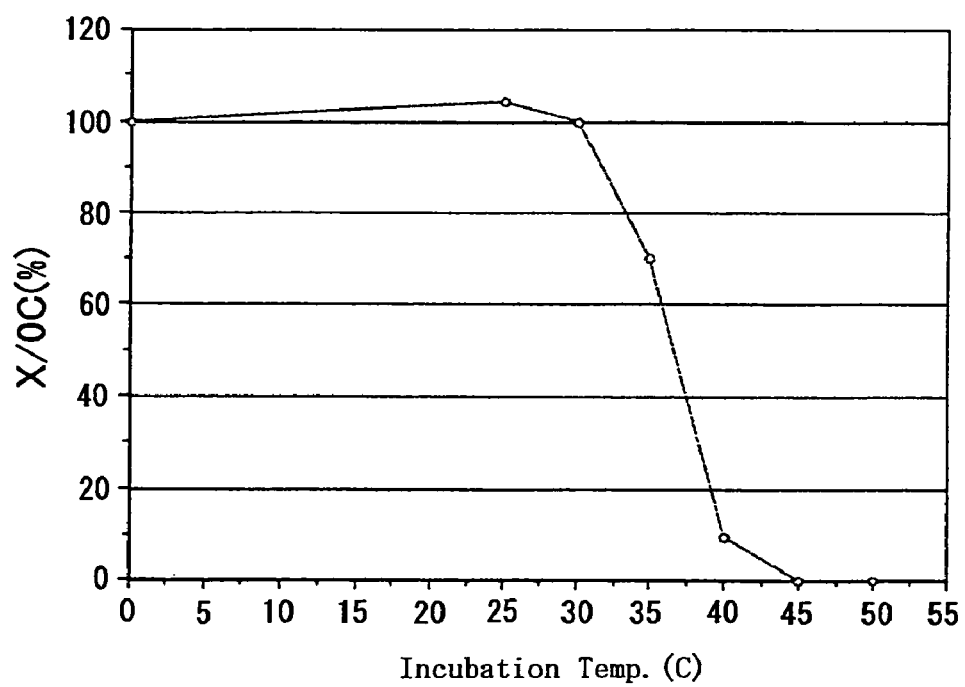
FIG. 4 is a graph showing thermal stability of the N-methyl-L-phenylalanine dehydrogenase of the present invention.

The purified enzyme obtained in Example 5 was left at 25° C., 30° C., 35° C., 40° C., 45° C. and 50° C. for 30 minutes, and then measured for activity as in Example 7. The results are shown in FIG. 4 as remaining activity, with the activity of the untreated enzyme (left in ice) defined as 100. The enzyme according to the present invention showed 100% remaining activity up to 30° C.

Example 11

Substrate Specificity of the Present Enzyme When NADH is Used as the Coenzyme

Purified form of the present enzyme was obtained from cloned *Escherichia coli* cells in the same way as in Example 5.

Enzyme activity was measured by adding thereto various keto acids shown in Table 4 to a final concentration of 40 mM (except for β-phenylpyruvic acid, which was 30 mM), NADH to a final concentration of 0.3 mM, bis-Tris propane buffer (pH 10.0) to a final concentration of 100 mM, and methylamine to a final concentration of 180 mM, and examining the change in absorbance of the reaction solution at 340 nm. The reaction temperature during measurement was 37° C. Defining the activity of the enzyme when pyruvic acid was used as the substrate as 100%, the results are shown in Table 4 for relative activity.

TABLE 4

| Substrate | Relative activity |
|---|---|
| pyruvic acid | 100% |
| 2-ketohexanoic acid | 20% |
| 2-ketobutyric acid | 15% |
| 2-keto-n-valeric acid | 7.5% |
| β-fluoropyruvic acid | 4.2% |
| β-phenylpyruvic acid | 0% |

TABLE 5

| Amines | Relative activity |
|---|---|
| methylamine | 100% |
| ethylamine | 1.5% |
| N-propylamine | 1.1% |
| isopropylamine | 1.5% |
| dimethylamine | 1.4% |
| ammonium | 0% |
| cyclohexanamine | 1.3% |

Example 12

Measurement of Optimal pH When NADH is Used as the Coenzyme

Purified form of the present enzyme was obtained from cloned *Escherichia coli* cells in the same way as in Example 5.

Figure 5:
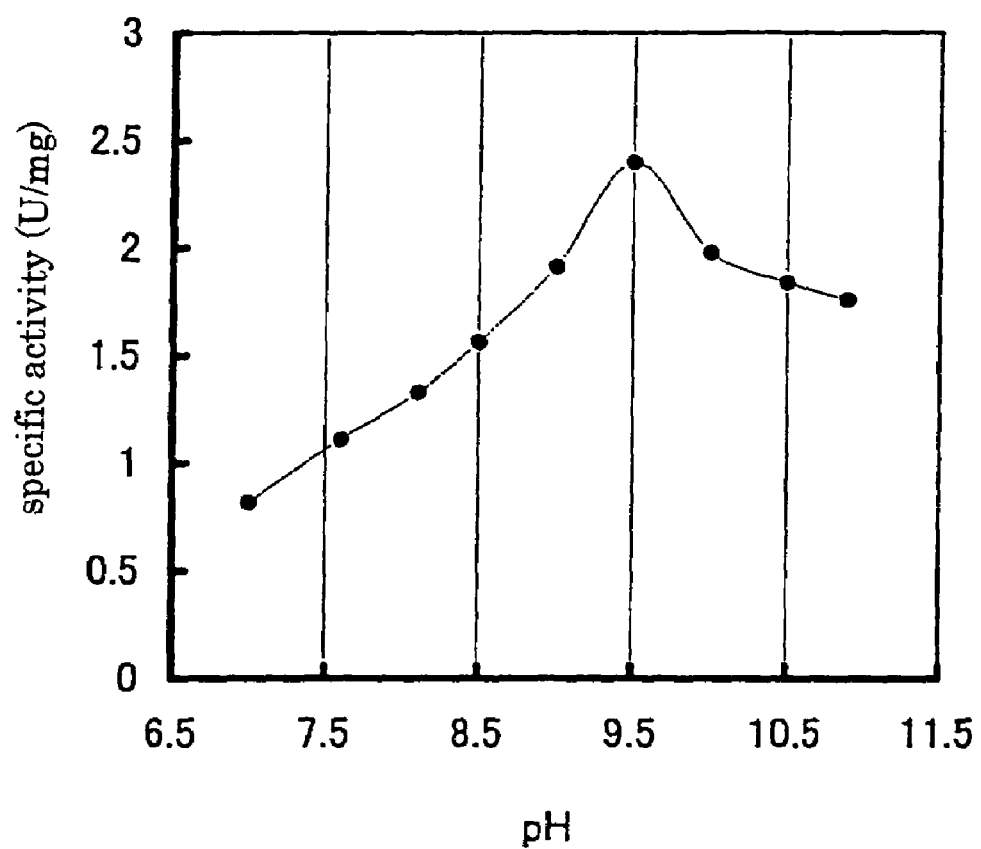
FIG. 5 is a graph showing the effect of pH on the N-methyl-L-phenylalanine dehydrogenase of the present invention.

Enzyme activity was measured by adding thereto pyruvic acid to a final concentration of 80 mM, NADH to a final concentration of 0.3 mM, and methylamine adjusted to various pH values with sulfuric acid to a final concentration of 180 mM, and examining the change in absorbance of the reaction mixture at 340 nm. The reaction temperature during measurement was 37° C. Defining the amount of enzyme that reacted with 1 micromole of pyruvic acid per minute as 1 unit, the results are shown in FIG. 5 for the relationship between the number of units per protein amount (u/mg) and pH. The optimal pH of the reaction was 9.5.

Example 13

Examination of Reverse Reaction When NAD is Used as the Coenzyme

Purified form of the present enzyme was obtained from cloned *Escherichia coli* cells in the same way as in Example 5.

Enzyme activity was measured by adding thereto N-methyl-L-alanine to a final concentration of 50 mM, NAD to a final concentration of 10 mM, and bis-Tris propane buffer (pH 10.0) to a final concentration of 100 mM, and examining the change in absorbance of the reaction mixture at 340 nm. The reaction temperature during measurement was 37° C. The activity was $7.8 \times 10^{-3}$ (u/mg of protein).

Example 14

Substrate Specificity of the Present Enzyme When NADPH is Used as the Coenzyme

Purified form of the present enzyme was obtained from cloned *Escherichia coli* cells in the same way as in Example 5.

Enzyme activity was measured by adding thereto various amines shown in Table 5 to a final concentration of 60 mM, NADPH to a final concentration of 0.2 mM, and β-phenylpyruvic acid to a final concentration of 10 mM, and examining the change in absorbance of the reaction solution at 340 nm. The reaction temperature during measurement was 37° C. Defining the activity of the enzyme when methylamine was used as the substrate as 100%, the results are shown in Table 5 for relative activity.

Example 15

Purification of DNA from *Bacillus subtilis* Strain

*Bacillus subtilis* strain was cultivated in LB medium to obtain cells. Chromosomal DNA was prepared from the cells using Qiagen kit (Qiagen) according to the method described in the attached manual.

Example 16

Cloning of Glucose Dehydrogenase Gene from *Bacillus subtilis* Strain

For regeneration of NADPH, the gene for glucose dehydrogenase (hereinafter abbreviated as GDH) of *Bacillus subtilis* strain described in literature (J.Bacteriol.166, 238–243 (1986)) was cloned. In order to clone only the open reading frame region of the GDH gene, primers BsuG_S (SEQ ID No. 6) and BsuG_A (SEQ ID No. 7) were synthesized based on the structure of the 5'- and 3'-terminals of the structural gene, based on the nucleotide sequence described in the literature. Using the chromosomal DNA of *Bacillus subtilis* strain prepared in Example 17 as the template, 30 cycles of PCR (94° C., 30 seconds; 54° C., 30 seconds; 72° C., 1 minute) were performed to obtain specifically amplified DNA. The DNA fragments obtained were digested with two restriction enzymes, EcoRI and HindIII. Plasmid vector pKK223-3 (Amersham-Pharmacia) was digested with EcoRI and HindIII, and the above PCR-amplified DNA fragments were ligated using T4 DNA ligase to obtain pKK223-3GDH. The nucleotide sequence of the inserted fragment was analyzed, and the all nucleotides matched the nucleotide sequence shown in the database (DDBJ Accession No. M12276). The nucleotide sequence of the GDH gene obtained is shown in SEQ ID No. 8. The nucleotide sequence shown in SEQ ID No. 8 encodes the polypeptide of SEQ ID No. 9.

Example 17

Construction of GDH Plasmid pSTV28-GDH which can be Co-expressed with pENMadh [Plasmid Where DNA Fragment of the Dehydrogenase of the Invention is Inserted into pET21a]

pKK223-3GDH which was constructed in Example 16 was digested with two different restriction enzymes, EcoRI and PstI and a fragment containing GDH gene of *Bacillus subtilis* strain was prepared. Plasmid vector pSTV28 (TAKARA Inc.) was digested with EcoRI and PstI, and the fragment containing the above GDH was ligated using T4 DNA ligase to obtain pSTV28-GDH.

Example 18

Co-Expression of GDH Derived from *Bacillus subtilis* Strain and the Dehydrogenase of the Invention in *Escherichia coli*

Cloned *Escherichia coli* BL21 (DE3) cells carrying pEN-Madh were transformed with pSTV28-GDH. Recombinant *Escherichia coli* was inoculated into liquid LB medium containing 100 μg/mL of ampicillin and 25 μg/mL of chloramphenicol, and cultivated for 17 hours. 1 mM of IPTG was then added, and cultivation was continued for additional 3 hours. Cells were collected, suspended in 20 mM Tris-HCl (pH 7.0), and ultrasonicated. Enzyme activity of the crude cellular extract obtained was measured.

(1) Measurement of Activity of the Present Dehydrogenase

Activity of the present dehydrogenase was measured in a reaction mixture containing 100 mM bis-trispropane buffer (pH 10.0), 0.2 mM NADPH, 30 mM methylamine, and 10 mM sodium pyruvate at 30° C. 1 U was defined as the amount of the enzyme capable of oxidizing 1 μmol of NADPH per minute under the above reaction conditions. The resulting activity was 6.6 U/mg of protein.

(2) Measurement of Activity of Glucose Dehydrogenase

Enzyme activity was measured by adding glucose to a final concentration of 100 mM, NADP to a final concentration of 2 mM, and Tris-hydrochloride buffer (pH 9.0) to a final concentration of 100 mM to 10 μl of crude enzyme, and examining the change in absorbance of 1 ml of the reaction mixture at 340 nm. The reaction temperature during measurement was 30° C. Defining the amount of enzyme that reacted with 1 micromole of glucose per minute as 1 unit, the number of units per protein amount (u/mg) was determined. The resulting activity was 3.4 U per 1 mg of protein.

Example 19

Synthesis of N-methyl-phenylalanine Using Glucose Dehydrogenase Co-expression Transformants

*Escherichia coli* obtained in Example 18 was cultivated as in Example 17 to obtain 100 ml of culture. After cultivation, cells were collected by centrifugation and washed twice with 40 ml of 20 mM Tris-hydrochloride buffer (pH 7.0) containing 0.85% sodium chloride to obtain resting cells.

To the resting cells obtained, a reaction solution containing sodium phenylpyruvate in a final concentration of 100 mM, NADP in a final concentration of 0.2 mM, glucose in a final concentration of 100 mM, and methylamine-hydrochloric acid (pH 9) in a final concentration of 700 mM was added to achieve cell turbidity of 20 (absorbance at 660 nm). The reaction was conducted while stirring at 30° C. and adjusting pH to 8 to 9 with 10 N aqueous sodium hydroxide solution. The amount of N-methylphenylalanine produced after 24 hours of reaction was 13.4 g/L (reaction yield=75%).

Example 20

Co-Reaction with D-Amino Acid Oxidase (1)

Purified form of the present enzyme was obtained from cloned *Escherichia coli* cells in the same way as in Example 10.

To 100 μl of the reaction solution, D-phenylalanine was added to a final concentration of 50 mM, NADPH to a final concentration of 10 mM, methylamine adjusted to pH 10 with sulfuric acid to a final concentration of 60 mM, and Tris-hydrochloride buffer (pH 9) to a final concentration of 100 mM, and then 0.052 units of D-amino acid oxidase (Sigma Corporation, derived from porcine kidney) was added. The protein amount of the present enzyme in the reaction solution was adjusted to 26.5 μg. The reaction temperature during measurement was 30° C.

At 900 minutes later, 25 μl of trichloroacetic acid was added to the reaction solution to achieve a final concentration of 2% and to terminate the reaction. The reaction solution was analyzed by HPLC under the following conditions.

Column: ODS column UK-C18 250×4.6 mM (Imtakt Corporation)
Eluant: water 100%
Flow rate: 0.5 ml/min
Temperature: 40° C.
Detection: UV 210 nm Results of measurement: 0.46 g/L of N-methylphenylalanine was produced. The amount of remaining phenylalanine was 1.06 g/L.

Example 21

Co-Reaction with D-amino Acid Oxidase (2)

Figure 6:
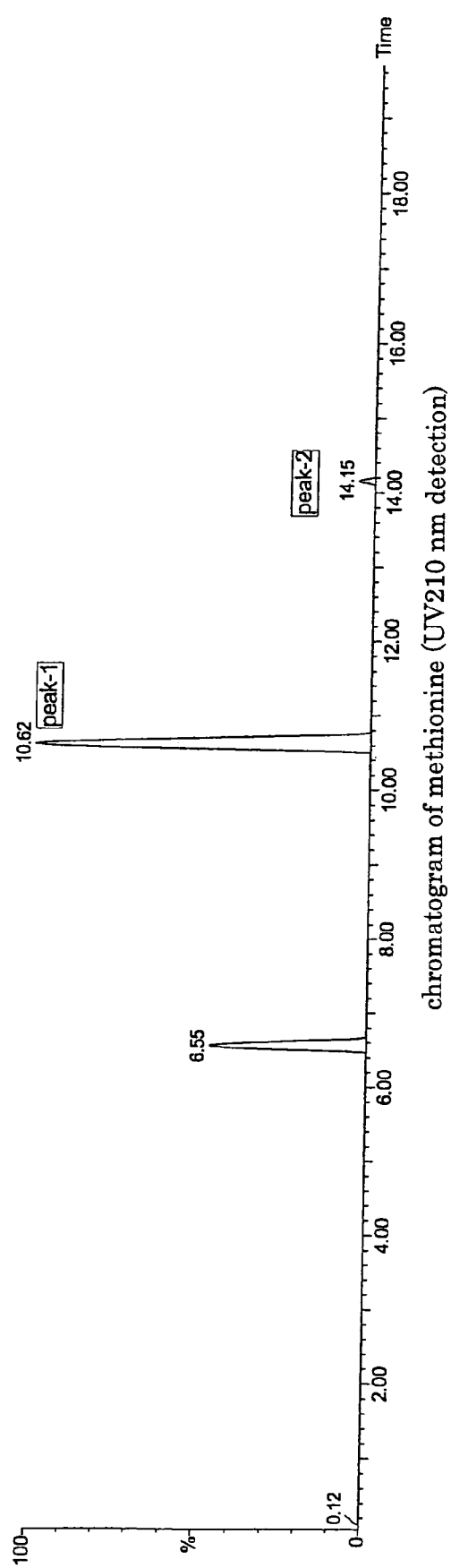
FIG. 6 shows the result of HPLC analysis of the product from co-reaction with D-amino acid oxidase.
Figure 7:
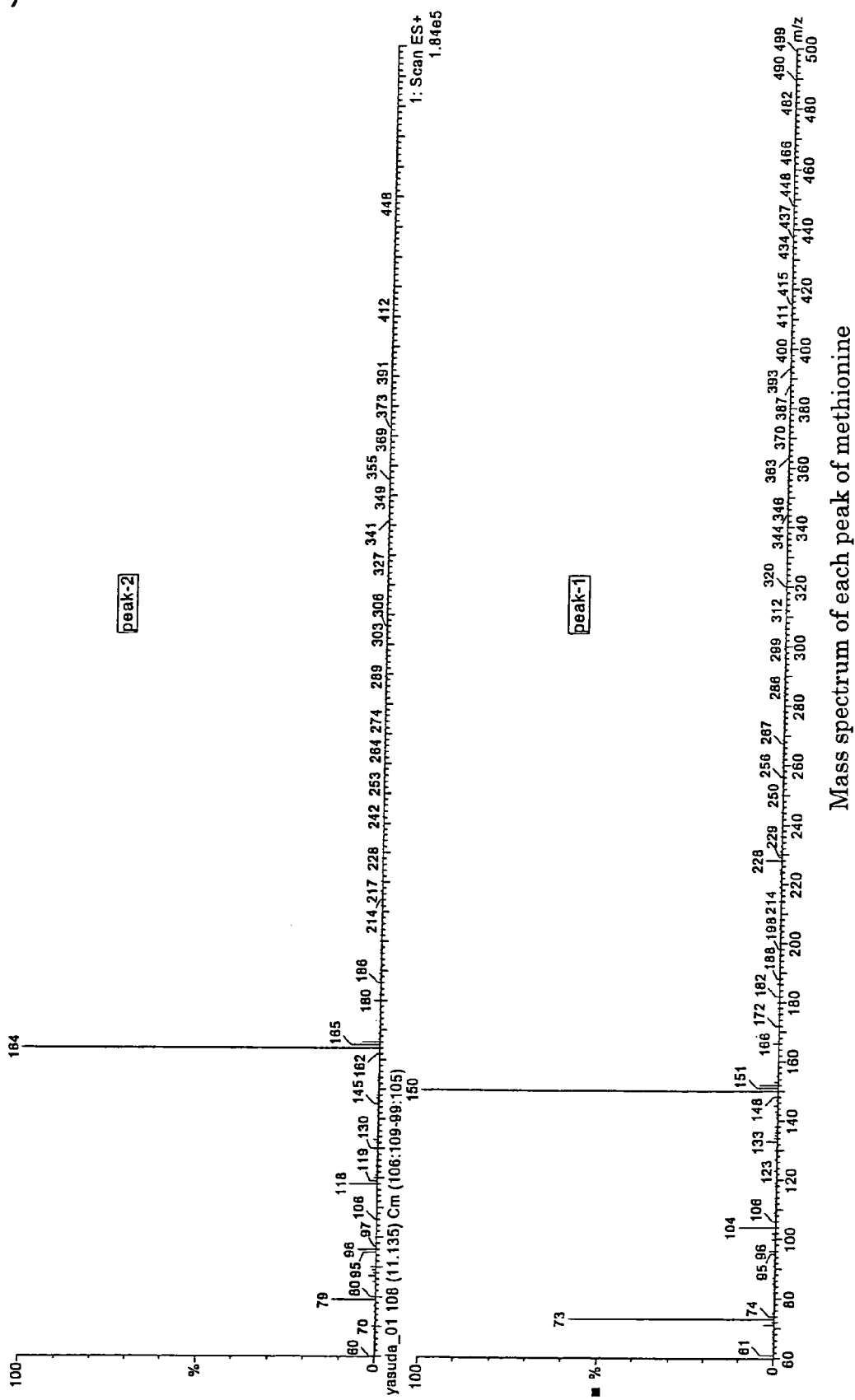
FIG. 7 shows the result of mass spectrometry analysis of peak-1 and peak-2 of FIG. 6.

This Example was carried out as in Example 20 except that D-methionine was used in place of phenylalanine. A chromatogram from HPLC is shown in FIG. 6. The HPLC retention time of methionine was 10.6 minutes, and a peak was formed at 14.1 minutes with the reaction. This peak was speculated to be N-methyl methionine. LC-mass was conducted using the same analytical column under the following conditions. The result of mass spectrometry is shown in FIG. 7. The peak which was speculated to be N-methyl methionine had a molecular weight of 163, which corresponds to the molecular weight of N-methyl methionine.

LC-mass conditions:
Device: Waters 2690 Separations Module and Micromass ZMD Mass Spectrometer
Column: ODS column UK-C18 250×4.6 mM (Imtakt Corporation)
Eluant: water 100%
Flow rate: 0.5 ml/min
Temperature: 40° C.
Detection: UV 210 nm
Ionization method: electrospray ionization method (ESI) positive ion detection
Mass scan condition: m/z 60 to 500, 1 sec
Applied voltage: 3.6 kV
Cone voltage: 10 V

Example 22

Co-reaction with L-phenylalanine Dehydrogenase

This Example was carried out as in Example 20, except that L-phenylalanine dehydrogenase (Sigma Corporation) was used in place of D-amino acid oxidases and L-phenylalanine was used in place of D-phenylalanine.

Result: 0.21 g/L of N-methylphenylalanine was produced. The amount of remaining L-phenylalanine was 2.75 g/L.

Example 23

Purified form of the present enzyme was obtained from cloned *Escherichia coli* cells in the same way as in Example 10.

To 14 μg of the present enzyme protein, methylpyruvic acid was added to a final concentration of 30 mM, NADPH to a final concentration of 10 mM, methylamine adjusted to pH 10 with sulfuric acid to a final concentration of 60 mM, phosphate buffer (pH 7) to a final concentration of 100 mM, and 100 μl of the reaction solution was allowed to react at 30° C. for 4 hours. Once the reaction was complete, HPLC analysis was conducted under the following conditions.
Column: CHIRALPAK WH 250×4.6 mM (Daicel)
Eluant: 2 mM CuSO$_4$
Flow rate: 0.5 ml/min
Temperature: 50° C.
Detection: UV 254 nm
Result: 0.1 g/L of N-methylalanine was produced.

Example 24

< Co-reaction with D-amino Acid Oxydase (1)>

A purified present enzyme of cloned *Escherichia coli* strain was obtained according to the same method as described in Example 5.

To this were added DL-pipecolic acids (manufactured by Tokyo Kasei Kogyo) at a final concentration of 50 mM, NADPH at a final concentration of 100 mM, and Tris hydrochloric acid buffer (pH 9) at a final concentration of 100 mM. To 100 μl of the resultant reaction liquid was added 0.052 unit of D-amino acid oxydase (manufactured by Sigma, derived from porcine kidney). At this time, the protein amount of the present enzyme was set to be 26.5 μg. The reaction temperature at measurement was set to be 30° C.

After 900 minutes, the reaction solution was added with 25 μl of trichloroacetic acid to give the final concentration of 2% to terminate the reaction.

The reaction liquid was analyzed by HPLC with the following conditions.
Column: CHIRALPAK WE 250×4.6 mm (manufactured by Daicel)
Eluant: 2 mM CuSO$_4$
Flow rate: 0.5 mL/min
Temperature: 50° C.
Detection: UV 254 nm
Measurement result showed that D-pipecolic acid had disappeared completely, and that 45 mM of L-pipecolic acid was generated.

Example 25

< Co-Reaction with D-amino Acid Oxydase (2)>

The same process as described in Example 24 was conducted except for using D-Proline in place of DL-pipecolic acids. After 600 minutes, D-Proline disappeared completely, and 45 mM of L-Proline was generated.

Example 26

<Synthesis of L-Pipecolic Acid by Using Glucose Dehydrogenase/N-methyl-L-amino Acid Dehydrogenase Co-expression Transformant>

The *Escherichia coli* obtained in Example 18 was cultivated in the same way as described in Example 18 to give 100 mL of culture fluid. After cultivation, fungal cells were collected by centrifugation and washed twice with 40 mL of 20 mM Tris-hydrochloride buffer (pH 7.0) containing 0.85% of sodium chloride to give resting cells.

The resting cells were once frozen to −80° C. The frozen fungal cells were added with 4 mL of 20 mM Tris-hydrochloride buffer (pH 7.0) to melt the fungal cells which was stirred strongly. To this was added PMSF to give the final concentration of 1 mM, and the mixture was subjected to ultrasonic disintegration, followed by centrifugation to give a crude enzyme liquid of protein concentration of 15 g/L.

The obtained crude enzyme liquid was added with a reaction liquid containing L-lysine (manufactured by Kishida Chemical) at a final concentration of 1%, NADP at a final concentration of 0.2 mM, glucose at a final concentration of 100 mM, FAD (manufactured by nacalai tesque) at a final concentration of 1 mM, L-lysine oxidase (manufactured by SEIKAGAKU CORPORATION) at a final concentration of 1.5 U/mL, catalase (manufactured by Sigma) at a final concentration of 14 U/mL, and Tris-hydrochloride buffer (pH 7.5) at a final concentration of 100 mM, thereby making the protein amount of the crude enzyme turn to 1.5 g/L. The total amount was set to be 10 mL. The reaction was conducted at 30° C. while adjusting the pH to 5.1 to 7.6 with 10 N aqueous sodium hydroxide solution under stirring.

After 5 hours, 0.5% of L-lysine, 7 U/mL of catalase and 100 mM of glucose were added, and the reaction was continued for additional 15 hours.

The reaction solution was analyzed by HPLC with the following conditions.
Column: CHIRALPAK WE 250×4.6 mm (manufactured by Daicel)
Eluant: 2 mM CuSO$_4$
Flow rate: 0.75 mL/min
Temperature: 50° C.
Detection: UV 254 nm
The concentration of L-pipecolic acid after the reaction for 15 hours was 14 g/L (reaction yield 98%). Further, no peak caused by D-pipecolic acid was found.

Example 27

<Synthesis of L-Hydroxyproline by Using Glucose Dehydrogenase/N-methyl-L-amino Acid Dehydrogenase Co-expression Transformant>

A crude enzyme solution was obtained in the same way as described in Example 26.

The obtained crude enzyme solution was added with a reaction solution containing cis-D-hydroxyproline (manufactured by Watanabe Kagaku) at a final concentration of 10 mM, NADP at a final concentration of 1 mM, glucose at a final concentration of 100 mM, FAD (manufactured by nacalai tesque) at a final concentration of 0.1 mM, D-amino acid oxidase (derived from Porcine kidney: manufactured by Wako) at a final concentration of 0.5 U/mL, catalase (manufactured by Sigma) at a final concentration of 50 U/mL and Tris-hydrochloride buffer (pH 8) at a final concentration of 100 mM, and the crude enzyme by an amount of one tenth. The total amount was set to be 0.2 mL. The reaction was conducted at 30° C. for 24 hours. At the same time, a solution containing no crude enzyme solution was also reacted.

The reaction solution was analyzed by HPLC with the following conditions.

Column: MCI GEL CRS 10W (4.6×500 mm) (manufactured by Mitsubishi Chemical)
Eluant: 0.4 mM $CuSO_4$
Flow rate: 0.5 ml/min
Temperature: 40° C.
Detection: UV 254 nm The result showed that 9.5 mM of L-hydroxyproline was generated in the reaction solution added with the crude enzyme solution, but no generation of L body was found in the reaction solution without addition of the crude enzyme solution.

Example 28

<Synthesis of L-Pipecolic Acid by Using Glucose Dehydrogenase/N-methyl-L-amino Acid Dehydrogenase Co-expression Transformant>

The same process as described in Example 27 was conducted by using D-lysine (manufactured by Tokyo Kasei), DL-pipecolic acids (manufactured by Tokyo Kasei) or D-ornthine (manufactured by Tokyo Kasei).

5.9 mM of L-pipecolic acid was generated from D-lysine, but no generation thereof was found in the reaction solution without addition of the crude enzyme.

10 mM of L-pipecolic acid was generated from DL-pipecolic acids, but no generation thereof was found in the reaction solution without addition of the crude enzyme.

Example 29

<Synthesis of L-Proline by Using Glucose Dehydrogenase/ N-methyl-L-amino Acid Dehydrogenase Co-expression Transformant>

6.8 mM of L-Proline was generated from D-ornithine, but generation thereof was also found in the reaction solution without addition of the crude enzyme, that is, 6.1 mM of L-Proline was generated. It is thought that Δ1-pyrrolidine 2-carboxylic acid generated by D-amino acid oxydase becomes spontaneously racemic Prolines, and the D-Proline receives again the action of D-amino acid oxydase to become Δ1-pyrrolidine 2-carboxylic acid, resulting in accumulation of L-Proline.

Example 30

<Synthesis of Optically Active Cyclic Amino Acid Containing a Sulfur Atom in the Ring and Optically Active Cyclic Amino Acid Containing an Oxygen Atom in the Ring from Diamino Acid>

A crude enzyme solution was obtained in the same way as described in Example 26.

Reaction solutions prepared by adding NADP at a final concentration of 5.4 mM, glucose at a final concentration of 108 mM, FAD (manufactured by nacalai tesque) at a final concentration of 0.1 mM, L-lysine oxidase (manufactured by SEIKAGAKU CORPORATION) at a final concentration of 0.8 U/mL, catalase (Manufactured by Sigma) at a final concentration of 54 U/ml and Tris-hydrochloric acid buffer (pH 8.2) at a final concentration of 100 mM to each of L-lysine (manufactured by Kishida Chemical), aminoethyl-L-cysteine (manufactured by ICN) and (S)-(+)-2-Amino-3-(2-amino ethoxy)propanoic acid monohydrochrolide (manufactured by Aldrich) each at a final concentration of 10 mM, respectively, were added with the crude enzyme by one tenth volume, respectively. The total amount of each solution was set to be 0.2 mL. The reaction was conducted at 30° C. for 24 hours. At the same time, solutions without addition of the crude enzyme solution were also allowed to react as the control.

The reaction solutions were analyzed by HPLC with the following conditions.
Column: MCI GEL CRS10W (4.6×500 mm) (manufactured by Mitsubishi Chemical)
Eluant: 0.4 mM $CuSO_4$
Flow rate: 0.5 mL/min
Temperature: 40° C.
Detection: UV 254 nm As a result, 9.9 mM of L-pipecolic acid was generated from L-lysine, but no generation thereof was found in the control without addition of the crude enzyme.

In the sample prepared by adding the crude enzyme solution to aminoethyl cysteine, a peak generated at a retention time of 12.1 minutes, but no generation of this peak was found in the sample without addition of the crude enzyme solution.

The present product is thought to be L-3-thiomorpholine carboxylic acid (R-3-thiomorpholine carboxylic acid), which is a L-cyclic amino acid generated according to the following reaction formula.

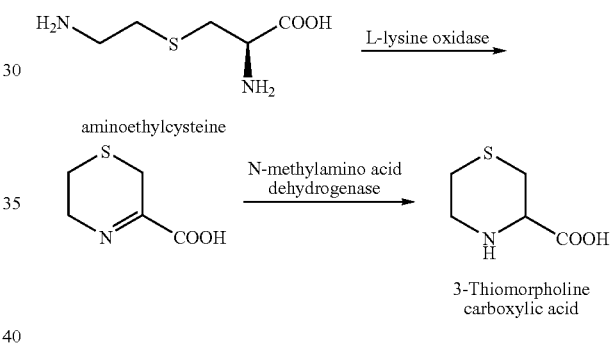

In the sample prepared by adding the crude enzyme solution to 2-amino-3-(2-amino ethoxy)propanoic acid, a peak generated at a retention time of 7.8 minutes, but no generation of this peak was found in the sample without addition of the crude enzyme solution.

The present product is thought to be L-3-morpholine carboxylic acid, which is a L-cyclic amino acid generated according to the following reaction formula.

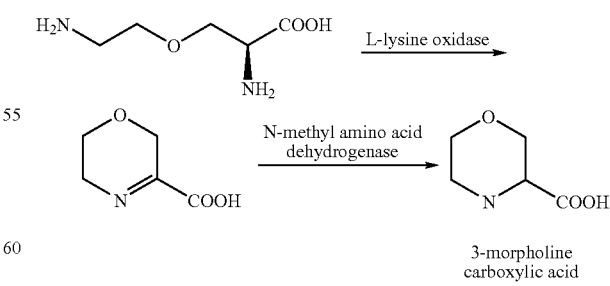

Example 31

<Confirmation of the Product by LC-Mass>

In order to confirm the 3-thiomorpholine carboxylic acid and 3-morpholine carboxylic acid generated in Example 30, purification and analysis by using LC-Mass were conducted.

Study of conditions for separating cyclic amino acids from amino acid as raw material by using silica gel TLC (manufactured by Merck, 1.05715) taught that use of a developing liquid of methanol:water:acetonitrile=1:1:4 allows amino acid as raw material to stay at the starting point and cyclic amino acids to be developed, thereby enabling us to separate them effectively. Further, coloring with ninhydrin leads cyclic amino acids to be of a characteristic color, thereby enabling us to distinguish them from usual amino acid. For example, under this condition, pipecolic acid is colored purple at Rf=0.22, Proline is colored yellow at Rf=0.20. Analysis of the reaction solution of aminoethyl cysteine in Example 30 under the condition showed a colored spot of pale ultramarine at Rf=0.32. Analysis of the reaction solution of 2-amino-3-(2-amino ethoxy)propanoic acid under the condition showed a colored spot of magenta at Rf=0.23.

Respective reaction solutions were spotted to a PLC plate (manufactured by Merck, ART13793) and dried sufficiently, followed by development with a developing liquid of a composition of methanol:water:acetonitrile=1:1:4. A part of the plate was cut off and colored with ninhydrin to confirm the position of the target. The relevant part was scratched up, eluted with methanol, from which silica gel was removed by filter paper, and the methanol eluate was concentrated. The concentrate was dissolved with a small amount of water and added with hydrochloric acid to be acidic, followed by being adsorbed to a strongly acidic cation-exchange resin (manufactured by Mitsubishi Chemical, SK1B) which had been regenerated to H-type. The resin was washed with distilled water and eluted with 1 N aqueous ammonia. The eluate was concentrated and dissolved with a small amount of methanol. After confirming that the cyclic amino acid part had been purified by TLC, LC-Mass analysis was conducted under the following conditions.

LC-Mass apparatus: manufactured by Hewlett-Packard, 1100MSD
HPLC Column: manufactured by Imtakt, UK-C18 (250×4.6 mm)
Eluant: 10% acetonitrile
Flow rate: 0.5 mL/min
Temperature: 40° C.
Pressure: 91 bar
UV 210 nm
Ionization voltage: 20V
Ionization method: API-ES method
Cation-measuring mode In the analysis of the sample purified from the reaction solution of aminoethyl cysteine, the peak at retention time of 6.8 represented a molecular ion of m/z 148.1. Since one proton has been added, molecular weight of the compound is 147.1, which coincides with the molecular weight of 3-thiomorpholine carboxylic acid.

In the analysis of the sample purified from the reaction solution of 2-amino-3-(2-amino ethoxy)propanoic acid, the peak at retention time of 5.7 represented a molecular ion of m/z 132.1. Since one proton has been added, molecular weight of the compound is 131.1, which coincides with the molecular weight of 3-morpholine carboxylic acid.

Example 32

<Generation Reaction of azepane-2-carboxylic acid from L-Homolysine>

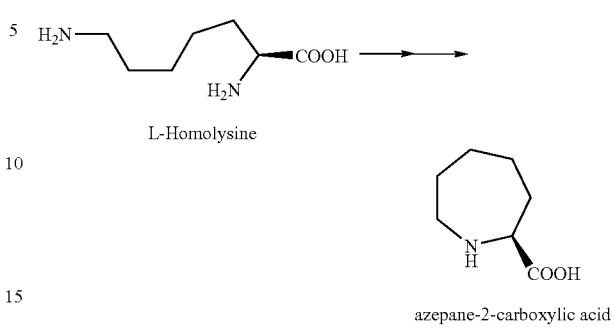

L-Homolysine was synthesized by using a publicly known method (JP-A-60-218400).

The reaction was conducted in the same way as described in Example 30. The resultant was purified in the same way as Example 31 and analyzed with TLC and LC-Mass. In TLC, it was colored brown at Rf=0.28. In LC-Mass, the peak of a molecular ion of m/z 145.10 was confirmed at rt=7.17. This coincides with the value obtained by adding a proton to the molecular weight 144.10 of azepane-2-carboxylic acid. Further, measurement with H-NMR gave the same value as that described in a publicly known document (Liebigs Ann. Chem 1989, pp 11215–1232).

Example 33

<Generation Reaction of 4-hydroxypipecolic acid from 5-hydroxy-DL-lysines>

5-hydroxy-DL-lysines used were manufactured by Aldrich.

The reaction was conducted in the same way as Example 23. The resultant was purified in the same way as Example 24 and analyzed with TLC and LC-Mass. In TLC, it was colored violet similar to the case with pipecolic acid at Rf=0.26. In LC-Mass, the peak of a molecular ion of m/z 146.20 was confirmed at rt=5.64. This coincides with the value obtained by adding a proton to the molecular weight 145.16 of 4-hydroxypipecolic acid. Further, measurement with H-NMR gave the same value as that described in a publicly known document (Bull. Soc. Chim. Belg. vol91 (1982) pp 713–723).

The present product is thought to be L-4-hydroxypipecolic acid, which is a L-cyclic amino acid, generated according to the following reaction formula.

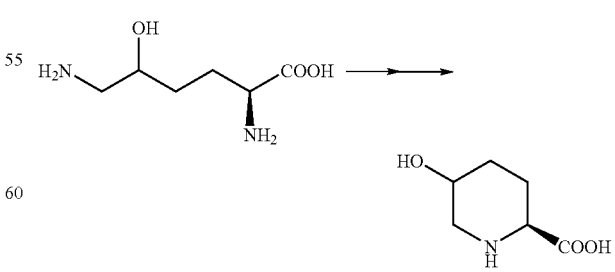

Example 34

<Generation Reaction of [1,4]thiazepane-3-carboxylic acid from aminopropyl-L-cystein>

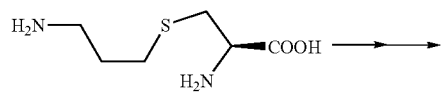

aminopropyl-L-cysteine

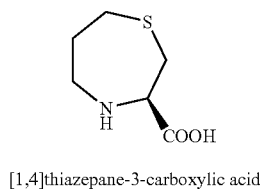

[1,4]thiazepane-3-carboxylic acid

Aminopropyl-L-cysteine was synthesized from L-cysteine and bromopropylamine by using a publicly known method (DE2217895).

The reaction was conducted in the same way as described in Example 30. The resultant was analyzed with TLC and LC-Mass in the same way as described in Example 31. In TLC, it was colored magenta at Rf=0.30. In LC-Mass, the peak of a molecular ion of m/z 162.10 was confirmed at rt=6.9. This coincides with the value obtained by adding a proton to the molecular weight 161.10 of [1,4]thiazepane-3-carboxylic acid.

Example 35

<Identification of [1,4]thiazepane-3-carboxylic acid>

A crude enzyme solution was obtained in the same way as described in Example 26.

10 mL of a reaction solution containing aminopropyl-L-cysteine at a final concentration of 85 mM, FAD (manufactured by nacalai tesque) at a final concentration of 0.1 mM, L-lysine oxidase (manufactured by SEIKAGAKU CORPORATION) at a final concentration of 0.65 U/ml, catalase (Manufactured by Sigma) at a final concentration of 123 U/ml, and Tris-hydrochloride buffer (pH 8.2) at a final concentration of 100 mM was stirred at room temperature for 5 hours. The solution was added with 1 mL of the crude enzyme, NADP at a final concentration of 1 mM, glucose at a final concentration of 233 mM. The reaction was conducted at 28° C. for 3 days.

The resultant was added with 10 mL of methanol, 30 mL of acetonitrile and 1 g of active carbon and stirred well, followed by centrifugation. The supernatant was filtrated with a filter of 0.20 μm and concentrated. The resultant was purified by PLC and SK1B in the same way as Example 24. The purified sample was dissolved with a small amount of methanol, to which acetone was added for crystallization. The crystal was white. The crystallized sample was analyzed with $^1$H-NMR and $^{13}$C-NMR.

$^1$H-NMR (400 MHz, D$_2$O): d=4.01 (1H, t, J=6.3), 3.19–3.45 (3H, m), 3.10 (1H, dd, J=15.9, 6.8), 2.63–2.82 (2H, m), 2.14 (2H, dt, J=10.9, 5.1) $^{13}$C-NMR (100 MHz, D$_2$O): d=31.9, 34.2, 34.5, 46.3, 64.8, 175.0

From the data, it was confirmed to be [1,4]thiazepane-3-carboxylic acid.

In addition, in order to obtain a further evidence, mass spectrometric measurement of a high resolution was conducted as follows.
Ionization method: DEI (+)
JEOL JMS-700 mass spectrometer
Scan Mode: EF
Reference substance: PFK As the result, molecular weight of 161.0509 (Err-mmu-0.1) and molecular composition of C6H11 O2 N1 S1 were measured. This is the composition formula that indicates the construction identified by the NMR analysis.

Example 36

<Identification of L-3-morpholine carboxylic acid>

A crude enzyme solution was obtained in the same way as in Example 26.

159 mg of L-aminoethylserine (manufactured by Wako) was dissolved in 6 mL of distilled water, and then 0.5 mL of 12.5 U/mL L-lysine oxidase (manufactured by SEIKAGAKU CORPORATION) containing 1 mM of FAD (manufactured by nacalai tesque), 1175 units of catalase (manufactured by Sigma) and 1 mL of 1M Tris-hydrochloride buffer (pH 8.2) were added thereto. The solution was stirred at 28° C. for a day. Then, the solution was added with 1 mL of the crude enzyme, 0.2 mL of 50 mM NADP and 0.8 mL of 50% glucose, and the mixture was allowed to react at room temperature. After 7 hours, the solution was added with 0.4 mL of an L-lysine oxidase solution, and allowed to react for additional 5 days.

The resultant was added with 20 mL of methanol, 20 mL of acetonitrile and 1 g of active carbon, and the mixture was stirred well, followed by centrifugation. The supernatant was filtrated with a filter of 0.20 μm and concentrated. The resultant was purified by PLC and SK1B in the same way as in Example 24. The purified sample was dissolved with a small amount of methanol, and acetone was added thereto for crystallization. The crystal was white. The crystallized sample was analyzed with $^1$H-NMR.

$^1$H-NMR (400 MHz, D$_2$O): d=4.04 (1H, dd, J=11.6, 3.0 Hz), 3.82 (1H, dt, J=12.4, 3.6 Hz), 3.55–3.67 (3H, m), 3.13 (1H, dt, J=13.1, 3.0 Hz), 2.98 (1H, ddd, J=13.4, 10.1, 0.9 Hz)

From the data, it was confirmed to be L-3-morpholine carboxylic acid.

INDUSTRIAL APPLICABILITY

According to the present invention, a novel dehydrogenase is provided which has properties different from known dehydrogenases. By using the dehydrogenase of the present invention, N-alkyl amino acids which are useful as intermediate materials for medicament or agricultural chemicals can be produced.

Further, according to the present invention, it is possible to provide a method of producing industrially inexpensive and highly pure various optically active cyclic amino acids by obtaining a cyclic amino acid having a double bond at 1-site as an intermediate from diamino acid or racemic cyclic amino acids that are industrially inexpensive, and then reducing the cyclic amino acid by using N-methyl-L-amino acid dehydrogenase.

Examples of the well known amino acid as optically active cyclic amino acids include, as shown by the following chemical formulae, 5-membered amino acids such as L-Proline and L-hydroxyproline, 6-membered amino acid such as L-Pipecolic acid, and 4-membered amino acid such as Azetidine-2-carboxylic acid. They are useful substances that are attracting attention as an intermediate for medical drugs or agricultural chemicals.

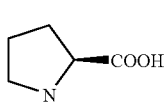
L-Proline

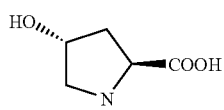
L-Hydroxyproline

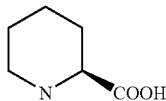
L-pipecolic acid

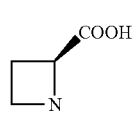
Azetidine-2-carboxylic acid

In addition, L-Thioproline, L-3-Morpholine carboxylic acid, L-3-Thiomorpholine carboxylic acid and the like, which are of heterocycles, are also mentioned as substances useful as an intermediate for medical drugs or agricultural chemicals.

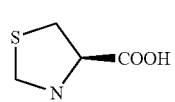
L-Thioproline

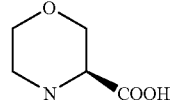
L-3-Morpholine carboxylic acid

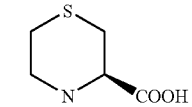
L-3-Thiomorpholine carboxylic acid

For example, as for drugs relevant to derivatives of pipecolic acid, which is a 6-membered cycle, Palinavir represented by the following chemical formula:

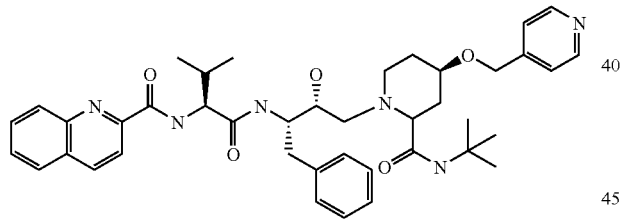

Selfotel represented by the following chemical formula:

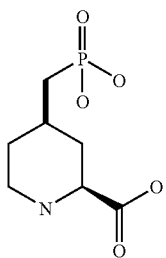

Argatroban represented by the following chemical formula:

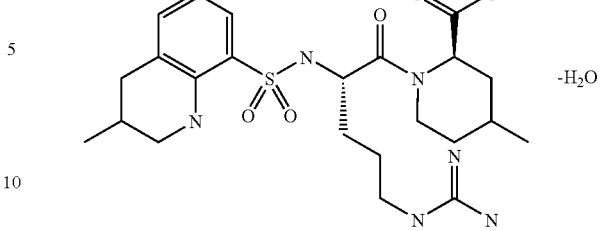

are known (Terence P Keenan et al, Tetrahedron asymmetry vol. 10 (1999) p 4331–4341).

Further, a derivative of pipecolic acid is utilized as a TNF-α converting enzyme inhibitor (Michael A Latavic et al, Bioorganic & Medicinal Chemistry Letters (2002) vol. 12, pp 1387–1390).

Furthermore, as for a drug relevant to a derivative of proline, Zefenopril represented by the following chemical formula and the like are known:

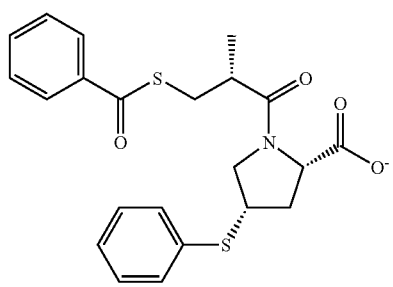

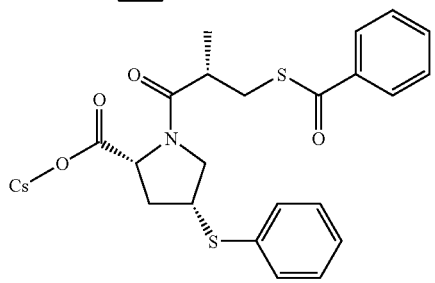

(J Med Chem (1988) vol. 31 p 1148)

As for drugs relevant to a derivative of azetidine carboxylic acid, nicotianamine represented by the following chemical formula as a gelatinase inhibitor:

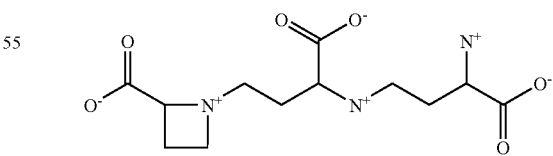

(Suzuki K et al, J antibiot (1996) vol. 49 p 1284-), or BMS-262084 represented by the following chemical formula as an antasthmatic:

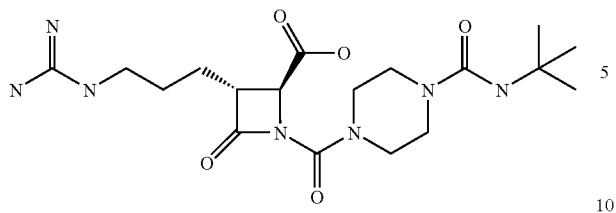

can be mentioned (Sutton J C et al, Bioorg Med Chem Lett. 2002 12(21) p 3229-33).

As for a heterocycle, for an antiinflammatory drug Z-4003 (EP0254354):

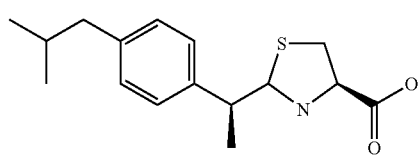

thioproline is used.

```
                        SEQUENCE LISTING

<160> NUMBER OF SEQ ID NOS: 9

<210> SEQ ID NO 1
<211> LENGTH: 341
<212> TYPE: PRT
<213> ORGANISM: Pseudomonas putida

<400> SEQUENCE: 1

Met Ser Ala Pro Ser Thr Ser Thr Val Val Arg Val Pro Phe Thr Glu
1               5                   10                  15

Leu Gln Ser Leu Leu Gln Ala Ile Phe Gln Arg His Gly Cys Ser Glu
            20                  25                  30

Ala Val Ala Arg Val Leu Ala His Asn Cys Ala Ser Ala Gln Arg Asp
        35                  40                  45

Gly Ala His Ser His Gly Val Phe Arg Met Pro Gly Tyr Val Ser Thr
    50                  55                  60

Leu Ala Ser Gly Trp Val Asp Gly Gln Ala Thr Pro Gln Val Ser Asp
65                  70                  75                  80

Val Ala Ala Gly Tyr Val Arg Val Asp Ala Ala Gly Gly Phe Ala Gln
                85                  90                  95

Pro Ala Leu Ala Ala Arg Glu Leu Leu Val Ala Lys Ala Arg Ser
            100                 105                 110

Ala Gly Ile Ala Val Leu Ala Ile His Asn Ser His His Phe Ala Ala
        115                 120                 125

Leu Trp Pro Asp Val Glu Pro Phe Ala Glu Glu Gly Leu Val Ala Leu
    130                 135                 140

Ser Val Val Asn Ser Met Thr Cys Val Val Pro His Gly Ala Arg Lys
145                 150                 155                 160

Pro Leu Phe Gly Thr Asn Pro Ile Ala Phe Ala Ala Pro Cys Ala Glu
                165                 170                 175

His Asp Pro Ile Val Phe Asp Met Ala Thr Ser Ala Met Ala His Gly
            180                 185                 190

Asp Val Gln Ile Ala Ala Arg Ala Gly Gln Gln Leu Pro Glu Gly Met
        195                 200                 205

Gly Val Asp Ala Asp Gly Gln Pro Thr Thr Asp Pro Lys Ala Ile Leu
    210                 215                 220

Glu Gly Gly Ala Leu Leu Pro Phe Gly Gly His Lys Gly Ser Ala Leu
225                 230                 235                 240

Ser Met Met Val Glu Leu Leu Ala Ala Leu Thr Gly Gly His Phe
                245                 250                 255
```

```
Ser Trp Glu Phe Asp Trp Ser Gly His Pro Gly Ala Lys Thr Pro Trp
            260                 265                 270

Thr Gly Gln Leu Ile Ile Val Ile Asn Pro Gly Lys Ala Glu Gly Glu
            275                 280                 285

Arg Phe Ala Gln Arg Ser Arg Glu Leu Val Glu His Met Gln Ala Val
            290                 295                 300

Gly Leu Thr Arg Met Pro Gly Glu Arg Tyr Arg Glu Arg Glu Val
305                 310                 315                 320

Ala Glu Glu Glu Gly Val Ala Val Thr Glu Gln Leu Gln Gly Leu
                325                 330                 335

Lys Glu Leu Leu Gly
            340

<210> SEQ ID NO 2
<211> LENGTH: 1026
<212> TYPE: DNA
<213> ORGANISM: Pseudomonas putida

<400> SEQUENCE: 2
atgtccgcac cttccaccag caccgttgtg cgcgtgcctt ttaccgagct gcaaagcctg      60
ttgcaggcca ttttccagcg ccatgggtgc agcgaggccg tggcccgggt gctggcccac    120
aactgcgcca cgcccagcg tgatggcgcc catagccatg gggtgttccg catgcccggt    180
tatgtctcga ccttggccag cggctgggtc gatggccagg ccacgccaca ggtcagcgac    240
gtggccgccg gctatgtgcg tgtcgatgct gcgggcggtt ttgcccagcc agcactggcg    300
gcggcccgtg agctgttggt ggcgaaggcg cgcagcgcag gcattgccgt gctggcgatc    360
cacaactcgc accacttcgc cgcgctatgg ccggatgtcg agccgttcgc cgaagagggc    420
ctggtagccc tcagcgtggt caacagcatg acctgcgtgg tgccgcatgg tgcacgcaag    480
ccgctgttcg gtaccaaccc catcgctttt gctgcgcctt cgccgagca tgacccgatc    540
gttttcgaca tggccaccag tgccatggcc catggcgatg tgcagattgc cgcgcgcgcc    600
ggccagcaat tgccggaggg catggggtg atgccgatg ccagccgac accgacccg        660
aaggcgatcc tggaaggcgg cgccctgctg ccatttggcg gcacaaggg ctcggcgttg    720
tcgatgatgg tcgagctgct ggcggcggcg ctgaccggcg gtcatttctc ctgggagttc    780
gattggtccg gcatccgggg gcgaaaacg ccatggaccg gcagttgat catcgtcatc       840
aacccaggca aggccgaggg cgagcgcttt gcccagcgca gccgcgagct ggtggagcac    900
atgcaggcgg tggggctgac gcgcatgccg ggcgagcggc gctaccgtga gcgcgaggtg    960
gccgaggagg aggggtggc ggtgaccgag caggagttgc aaggcctgaa agagctgctt    1020
ggctga                                                              1026

<210> SEQ ID NO 3
<211> LENGTH: 16
<212> TYPE: PRT
<213> ORGANISM: Pseudomonas putida

<400> SEQUENCE: 3

Ala Phe Ser Thr Ser Thr Val Val Arg Val Pro Phe Thr Glu Lys Gln
1               5                   10                  15

<210> SEQ ID NO 4
<211> LENGTH: 35
<212> TYPE: DNA
<213> ORGANISM: Artificial Sequence
<220> FEATURE:
```

<223> OTHER INFORMATION: synthetic DNA

<400> SEQUENCE: 4
ggaattccat atgtccgcac cttccaccag caccg                              35

<210> SEQ ID NO 5
<211> LENGTH: 31
<212> TYPE: DNA
<213> ORGANISM: Artificial Sequence
<220> FEATURE:
<223> OTHER INFORMATION: synthetic DNA

<400> SEQUENCE: 5
gggaagcttt cagccaagca gctctttcag g                                  31

<210> SEQ ID NO 6
<211> LENGTH: 28
<212> TYPE: DNA
<213> ORGANISM: Artificial Sequence
<220> FEATURE:
<223> OTHER INFORMATION: synthetic DNA

<400> SEQUENCE: 6
cggaattcat gtatccggat ttaaaagg                                      28

<210> SEQ ID NO 7
<211> LENGTH: 23
<212> TYPE: DNA
<213> ORGANISM: Artificial Sequence
<220> FEATURE:
<223> OTHER INFORMATION: synthetic DNA

<400> SEQUENCE: 7
gcaagcttat taaccgcggc ctg                                           23

<210> SEQ ID NO 8
<211> LENGTH: 783
<212> TYPE: DNA
<213> ORGANISM: Bacillus subtilis

<400> SEQUENCE: 8
atgtatccgg atttaaaagg aaaagtcgtc gctattacag gagctgcttc agggctcgga    60
aaggcgatgg ccattcgctt cggcaaggag caggcaaaag tggttatcaa ctattatagt   120
aataaacaag atccgaacga ggtaaaagaa gaggtcatca aggcgggcgg tgaagctgtt   180
gtcgtccaag gagatgtcac gaaagaggaa gatgtaaaaa atatcgtgca acggcaatt   240 aaggagttcg gcacactcga tattatgatt aataatgccg gtcttgaaaa tcctgtgcca   300
tctcacgaaa tgccgctcaa ggattgggat aaagtcatcg gcacgaactt aacgggtgcc   360
tttttaggaa gccgtgaagc gattaaatat ttcgtagaaa acgatatcaa gggaaatgtc   420
attaacatgt ccagtgtgca gcgtttcct tggccgttat ttgtccacta tgcggcaagt   480
aaaggcggga taaagctgat gacagaaaca ttagcgttgg aatacgcgcc gaagggcatt   540
cgcgtcaata atattgggcc aggtgcgatc aacacgccaa tcaatgctga aaaattcgct   600
gaccctaaac agaaagctga tgtagaaagc atgattccaa tgggatatat cggcgaaccg   660
gaggagatcg ccgcagtagc agcctggctt gcttcgaagg aagccagcta cgtcacaggc   720
atcacgttat tcgcggacgg cggtatgaca caatatcctt cattccaggc aggccgcggt   780
taa                                                                 783

```
<210> SEQ ID NO 9
<211> LENGTH: 260
<212> TYPE: PRT
<213> ORGANISM: Bacillus subtilis

<400> SEQUENCE: 9

Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Val Gln Gly
    50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
            100                 105                 110

Ile Gly Thr Asn Leu Thr Gly Ala Phe Leu Gly Ser Arg Glu Ala Ile
        115                 120                 125

Lys Tyr Phe Val Glu Asn Asp Ile Lys Gly Asn Val Ile Asn Met Ser
    130                 135                 140

Ser Val His Ala Phe Pro Trp Pro Leu Phe Val His Tyr Ala Ala Ser
145                 150                 155                 160

Lys Gly Gly Ile Lys Leu Met Thr Glu Thr Leu Ala Leu Glu Tyr Ala
                165                 170                 175

Pro Lys Gly Ile Arg Val Asn Asn Ile Gly Pro Gly Ala Ile Asn Thr
            180                 185                 190

Pro Ile Asn Ala Glu Lys Phe Ala Asp Pro Lys Gln Lys Ala Asp Val
        195                 200                 205

Glu Ser Met Ile Pro Met Gly Tyr Ile Gly Glu Pro Glu Glu Ile Ala
    210                 215                 220

Ala Val Ala Ala Trp Leu Ala Ser Lys Glu Ala Ser Tyr Val Thr Gly
225                 230                 235                 240

Ile Thr Leu Phe Ala Asp Gly Gly Met Thr Gln Tyr Pro Ser Phe Gln
                245                 250                 255

Ala Gly Arg Gly
            260
```

The invention claimes is:

1. A cyclic amino acid, [1,4]thiazepane-3-carboxylic acid:

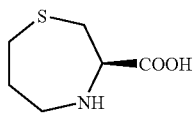

[1,4]tiazepane-3-carboxylic acid.

2. A method of producing L-cyclic amino acid, which comprises allowing N-methyl-L-amino acid dehydrogenase having the amino acid sequence of SEQ ID NO:1, or a cell containing the same, a lysate of the cell, or a culture solution obtained by culturing the cell, to act on a cyclic amino acid having a double bond at 1-site represented by the following formula (I):

wherein A represent an alkyl chain having a chain length of 1 to 6 atoms, which may include at least one hetero atom selected from the group consisting of a sulfur atom, an oxygen atom and a nitrogen atom in the chain or at the terminal thereof, and may be substituted, so as to generate an L-cyclic amino acid represented by the following formula (II):
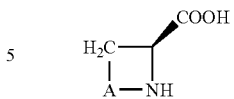
wherein A has the same meaning as described above.
* * * * *

UNITED STATES PATENT AND TRADEMARK OFFICE
CERTIFICATE OF CORRECTION

| | | |
|---|---|---|
| PATENT NO. | : 7,115,735 B2 | Page 1 of 1 |
| APPLICATION NO. | : 10/927028 | |
| DATED | : October 3, 2006 | |
| INVENTOR(S) | : Nobuyoshi Esaki et al. | |

It is certified that error appears in the above-identified patent and that said Letters Patent is hereby corrected as shown below:

On the Title page of the printed patent, at Item (56) References Cited, FOREIGN PATENT DOCUMENTS, insert
--JP 2001-190298 7/17/2001
WO 2/101003 12/19/2002--.

Signed and Sealed this

Fourth Day of December, 2007

JON W. DUDAS
*Director of the United States Patent and Trademark Office*